US010137085B2

(12) United States Patent
Huen et al.

(10) Patent No.: US 10,137,085 B2
(45) Date of Patent: Nov. 27, 2018

(54) NANOEMULSION FOR TRANSDERMAL DELIVERY AND METHOD OF MAKING THE SAME

(71) Applicant: Nano and Advanced Materials Institute Limited, Hong Kong (HK)

(72) Inventors: Ngar Yee Huen, Hong Kong (HK); Sau Kuen Connie Kwok, Hong Kong (HK); Jinjie Xu, Hong Kong (HK); Chun Him Wong, Hong Kong (HK); Min Xiao, Hong Kong (HK)

(73) Assignee: Nano and Advanced Materials Institute Limited, Hong Kong (HK)

(*) Notice: Subject to any disclaimer, the term of this patent is extended or adjusted under 35 U.S.C. 154(b) by 493 days.

(21) Appl. No.: 14/624,565

(22) Filed: Feb. 17, 2015

(65) Prior Publication Data

US 2015/0265533 A1 Sep. 24, 2015

Related U.S. Application Data

(60) Provisional application No. 61/967,454, filed on Mar. 19, 2014.

(51) Int. Cl.

| | |
|---|---|
| ***A61K 9/00*** | (2006.01) |
| ***A61K 9/06*** | (2006.01) |
| ***A61K 31/36*** | (2006.01) |
| ***A61K 38/18*** | (2006.01) |
| ***A61K 47/26*** | (2006.01) |
| ***A61K 9/107*** | (2006.01) |
| ***A61K 31/357*** | (2006.01) |

(52) U.S. Cl.

CPC .......... *A61K 9/1075* (2013.01); *A61K 9/0014* (2013.01); *A61K 9/06* (2013.01); *A61K 31/357* (2013.01); *A61K 31/36* (2013.01); *A61K 38/1808* (2013.01); *A61K 47/26* (2013.01)

(58) Field of Classification Search

None

See application file for complete search history.

(56) References Cited

U.S. PATENT DOCUMENTS

| | | | | |
|---|---|---|---|---|
| 2007/0036831 A1 | 2/2007 | Baker | | |
| 2007/0166255 A1* | 7/2007 | Gupta | A61K 8/31 | 424/70.1 |
| 2008/0317684 A1* | 12/2008 | Spann-Wade | A61K 9/0014 | 424/59 |
| 2009/0202654 A1* | 8/2009 | Nixon | A61K 8/985 | 424/574 |
| 2010/0055138 A1* | 3/2010 | Margulies | A61K 8/02 | 424/401 |

FOREIGN PATENT DOCUMENTS

| | | |
|---|---|---|
| CN | 102631405 A | 8/2012 |
| CN | 103040057 A | 4/2013 |
| EP | 1938801 A1 | 12/2006 |
| WO | WO2013138520 A1 * | 9/2013 |
| WO | WO2014153238 * | 9/2014 |

OTHER PUBLICATIONS

Office Action issued from the State Intellectual Property Office of the People's Republic of China dated May 2, 2017.

Sufeng Zhang & Hasan Uludag, Nanoparticulate Systems of Growth Factor Delivery, Pharmaceutical Research, Jul. 2009, pp. 1561-1580, vol. 26 No. 7, Springer Science & Business Media, New York.

Hua Nan, Liu Wei & Guo Rui-Chen, Development and Evaluation of Terpene Penetration Enhancers, China Journal of Chinese Materia Medica, Dec. 2008, pp. 2875-2881, vol. 33 Issue 24, China Academic Journal Electronic Publishing House, China.

Peter Clarysa, et al. In vitro percutaneous penetration through hairless rat skin: influence of temperature, vehicle and penetration enhancers, European Journal of Pharmaceutics and Biopharmaceutics 46 (1998) 279-283.

Hongzhuo Liu, et al. Investigation into the potential of low-frequency ultrasound facilitated topical delivery of Cyclosporin A, International Journal of Pharmaceutics 326 (2006) 32-38.

Keishiro Tomoda, et al. Enhanced transdermal permeability of estradiol using combination of PLGA nanoparticles system and iontophoresis, Colloids and Surfaces B: Biointerfaces 97 (2012) 84-89.

Yuqin Qiu, et al. Enhancement of skin permeation of docetaxel: A novel approach combining microneedle and elastic liposomes, Journal of Controlled Release 129 (2008) 144-150.

E. Touitoua, et al. Ethosomes—novel vesicular carriers for enhanced delivery: characterization and skin penetration properties, Journal of Controlled Release 65 (2000) 403-418.

Margarita Shumilov, et al. Buspirone transdermal administration for menopausal syndromes, in vitro and in animal model studies, International Journal of Pharmaceutics 387 (2010) 26-33.

Rozman Branka, et al. Simultaneous absorption of vitamins C and E from topical microemulsions using reconstructed human epidermis as a skin model, European Journal of Pharmaceutics and Biopharmaceutics 72 (2009) 69-75.

S. Peltola, et al. Microemulsions for topical delivery of estradiol, International Journal of Pharmaceutics 254 (2003) 99-107.

Yue Yuan, et al. Investigation of microemulsion system for transdermal delivery of meloxicam, International Journal of Pharmaceutics 321 (2006) 117-123.

M. Trotta, et. al. Influence of counter ions on the skin permeation of methotrexate from water-oil microemulsions, Pharmaceutics Acta Helvetiae 71 (1996) 135-140.

Varaporn Buraphacheep Junyaprasert, et. al. Enhancement of the Skin Permeation of Clindamycin Phosphate by Aerosol OT/1-Butanol Microemulsions Skin Permeation of Clindamycin Phosphate by Aerosol , Drug Development and Industrial Pharmacy, 33:874-880.

W. Dawson, et. al. Local Fundus Response to Blue (LED and Laser) and Infrared (LED and Laser) Sources, Exp. Eye Res. (2001) 73, 137±147.

(Continued)

*Primary Examiner* — Robert A Wax
*Assistant Examiner* — Randeep Singh
(74) *Attorney, Agent, or Firm* — Spruson & Ferguson (Hong Kong) Limited

(57) ABSTRACT

The present invention relates to a nanoemulsion for transdermal delivery. The presently claimed invention provides chemical formulations for preparing a nanoemulsion, and the methods for preparing the nanoemulsion. The nanoemulsion has desirable particle size for efficient transdermal delivery, and doesn't involve any organic solvent which is harmful to human skin. The corresponding fabrication method is simple.

18 Claims, 18 Drawing Sheets

(56) References Cited

OTHER PUBLICATIONS

Bei Li, et. al. Nanostructured Lipid Carriers Improve Skin Permeation and Chemical Stability of Idebenone, AAPS PharmSciTech, vol. 13, No. 1.
Lav Keshri, et. al. Development of thermodynamically stable nanostructured lipid carrier system using central composite design for zero order permeation of Econazole nitrate through epidermis, Pharmaceutical Development and Technology, 2013; 18(3): 634-644.
Julia C. Schwarz, et. al. Ultra-small NLC for improved dermal delivery of coenyzme Q10 , International Journal of Pharmaceutics 447 (2013) 213-217.
Yoshiro Tahara, et. al. A Solid-in-oil nanodispersion for transcutaneous protein delivery, Journal of Controlled Release 131 (2008) 14-18.
Fan Yang, et. al. Transdermal delivery of the anti-rheumatic agent methotrexate using a solid-in-oil nanocarrier, European Journal of Pharmaceutics and Biopharmaceutics 82 (2012) 158-163.
Philip J. Lee, et. al. Novel Microemulsion Enhancer Formulation for Simultaneous Transdermal Delivery of Hydrophilic and Hydrophobic Drugs, Pharmaceutical Research; Feb 2003; 20, 2.
Kam-Ming Ko, et. al. Schisandrin B Protects Against Tert-butylhydroperoxide Induced Cerebral Toxicity by Enhancing Glutathione Antioxidant Status in Mouse Brain, Molecular and Cellular Biochemistry 238: 181-186, 2002.
Po-Yee Chiu, et. al. Schisandrin B Decreases the Sensitivity of Mitochondria to Calcium Ioninduced Permeability Transition and Protects Against Ischemiareperfusion Injury in Rat Hearts, Acta Pharmacol Sin Oct. 2007; 28 (10): 1559-1565.
Philip Y. Lam, et. al. Schisandrin B Protects Against Solar Irradiation-induced Oxidative Stress in Rat Skin Tissue, Fitoterapia 82 (2011) 393-400.
Seung-Hee Ryu, et. al. Recombinant Human Epidermal Growth Factor Acceleratesthe Proliferation of Irradiated Human Fibroblastsand Keratinocytes in vitro and in vivo, J. Radiat. Res., 50, 545-552.
Richard E Fitzpatrick, et. al. Reversal of Photodamage With Topical Growth Factors: A Pilot Study, J Cosmetic & Laser Ther 2003; 5: 25-34.

* cited by examiner

NANOEMULSION FOR TRANSDERMAL DELIVERY AND METHOD OF MAKING THE SAME

CROSS REFERENCE TO RELATED APPLICATION

Pursuant to 35 U.S.C. § 119(e), this is a non-provisional patent application which claims benefit from U.S. provisional patent application Ser. No. 61/967,454 filed Mar. 19, 2014, and the disclosure of which is incorporated herein by reference.

FIELD OF THE INVENTION

The present invention relates to a nanoemulsion delivery system for transdermal delivery and method of making the same.

BACKGROUND

The skin, as the largest organ of the body, has long been considered as promising route for the administration of therapeutic agents. Since the skin is an excellent natural barrier against foreign substances, it is highly impermeable to therapeutic agents. In order to enhance skin permeability, scientists have tried many different penetration enhancement technologies, including adding chemical enhancer, sonophoresis, iontophoresis, and microneedle. Compare to aforementioned technologies, nano-vesicular delivery system obtains plenty of attentions due to various advantages, such as minimization of drug degradation and drug loss, increase of drug bioavailability and drug accumulation in the target area, prevention of harmful toxic effects, versatility and flexibility in handling drug with better patient compliance.

Nano-vesicular delivery system can broadly be classified into lipid based carriers and polymeric based colloidal carriers according to the basis of the main formulation component. These two families share the same advantages, such as controlled particle size, enhanced skin penetration and controlled release. The key difference between lipid and polymer based carriers is that the former are mainly composed of physiological lipids and hence they are more biocompatible, and can be degraded to non-toxic residues without safety issues caused by polymeric materials. Various lipid nano-carriers for skin care have been disclosed, such as liposome, ethosome, microemulsion, solid lipid nanoparticles (SLN), nanostructured lipid carriers (NLC) and solid-in-oil nano-dispersion. As such three types of lipid nano-vesicles, including microemulsion, NLC and solid-in-oil nanodispersions, are presented as examples in this invention to enhance skin penetration of either hydrophobic or hydrophilic active ingredients. These examples are given only for a better understanding of the present proposal, and not intended to limit the scope of the proposal in any way.

Microemulsions or nanoemulsions are thermodynamically stable isotropic dispersions, transparent, with low viscosity, consisting of oil and water stabilized by an interfacial film of surfactant molecules, typically in conjunction with a co-surfactant. The skin penetration-enhancing efficacy of the nanoemulsions can be attributed to the combined effect of both the lipophilic and the hydrophilic domains of the microemulsions. The lipid domain can directly partition into lipids of stratum corneum, or lipid vesicles themselves can intercalate between the lipid chains of the stratum corneum, thereby destabilizing its bilayer structure, leading to a pathway for drug penetration. On the other hand, the hydrophilic domain of the nanoemulsion can hydrate the stratum corneum to a greater extent leading to an increased passive percutaneous drug flux. As some lipid chains are covalently attached to the corneocytes, hydration of these proteins will also lead to the disorder of the lipid bilayers which further enhances the drug transport. Many studies have illustrated that microemulsion formulations possessed improved transdermal and dermal delivery properties for different drugs, such as estradiol, meloxicam, methotrexate and clindamycin phosphate. In order to achieve a better skin penetration of active ingredients, transdermal penetration enhancer incorporated nanoemulsion has been developed. V. Prasad Shastri' s group demonstrated a novel microemulsion system with oleyl alcohol and n-methyl pyrrolidone (NMP) as penetration enhancers to deliver two hydrophilic drugs (diltiazem HCl and lidocaine HCl) and two hydrophobic drugs (estradiol and lidocaine free base). A comparison between oil-in-water (o/w) with water-in-oil (w/o) nanoemulsion indicated that the former provides higher enhancement for both hydrophilic and hydrophobic drugs. The enhancement of drug permeability from the o/w microemulsion system is 17-fold for lidocaine free base, 30-fold for lidocaine HCl, 58-fold for estradiol, and 520-fold for diltiazem HCl when compared to aqueous solution.

Nanostructured lipid carriers (NLC) is derived from emulsions by simply replacing some the liquid lipid (oil) by a solid lipid, i.e. being solid at body temperature. There are five major advantages of NLC compared to other conventional carriers: (1) low toxicity and excellent tolerability due to the presence of physiological and biodegradable lipids; (2) small particle size which ensures a closer contact to the stratum corneum and increased skin penetration of drugs; (3) controlled release for many substances due to the solid matrix; (4) increased skin hydration effect due to the occlusive properties of lipid nanoparticles and (5) enhanced chemical stability of compounds which are sensitive to light, oxidation and hydrolysis. Due to the hydrophobic matrix, solid lipids particles have been widely used in deliver poor water soluble drugs to enhance their skin penetration and also the stability.

Solid-in-oil nanodispersion is another emulsion based delivery system. Typically, it is prepared by creating a water-in-oil emulsion followed by solvent and water removal. The resulted nanoparticles are dispersed in oil to form solid-in-oil nanodispersion which is comprised of active ingredient, surfactant and oil. Solid-in-oil nanodispersion has long been used in transdermal delivery for active ingredients, especially the hydrophilic proteins. Masahiro Goto's group has demonstrated that the skin penetration of insulin of 6 kDa, enhanced green fluorescent protein (EGFP) of 27 kDa and horseradish peroxidase (HRP) of 40 kDa could be enhanced in soild-in-oil nanodispersion compared to that of control. The same group also demonstrated that permeation efficiency through skin of an anti-rheumatic agent called methotrexate in solid-in-oil nanodispersion has a two- to three-fold increase compared to that of the control aqueous solution. Addition of urea as enhancer in the aforementioned dispersion achieves approximately 8.8-fold increase compared to that of the control aqueous solution after 24 h.

However, the abovementioned conventional technologies, especially lipid vesicle, have the disadvantages that their processing steps are complicated and they involve organic solvent which is harmful to human skin.

SUMMARY OF THE INVENTION

Accordingly, a first aspect of the presently claimed invention is to provide a chemical formulation for preparing a nanoemulsion.

According to an embodiment of the presently claimed invention, a chemical formulation for preparing a nanoemulsion comprises: an oil; a surfactant; ethanol; water; and an active ingredient; wherein a weight ratio of the water to the ethanol plus the oil and the surfactant is in a range of 3:7 to 2:8.

The ratio of the water to the ethanol plus the oil and the surfactant is a crucial technical feature since such ratio is able to reduce the size of the nanoemulsion down to below 100 nm, and this size range provides more efficient skin penetration. Additionally, this ratio can maximize the concentration of the encapsulation phase, and the carrier phase is maintained at the same time for providing higher transdermal delivery.

Preferably, a ratio of ethanol to oil to surfactant is about 1:1:2. Similarly, this ratio is also able to reduce the size of the nanoemulsion.

Preferably, the chemical formulation further comprises a penetration enhancer.

Preferably, the active ingredient is Schisandrin, or epidermal growth factor.

According to another embodiment of the presently claimed invention, a chemical formulation for preparing a nanoemulsion comprises: an oil; a surfactant; a penetration enhancer; water; and an active ingredient; wherein a weight ratio of the oil to the surfactant is in a range of 1:9 to 2:8.

The weight ratio of the oil to the surfactant is a crucial technical feature since such ratio is able to reduce the size of the nanoemulsion down to below 100 nm, providing higher skin penetration. Additionally, this ratio can maximize the concentration of the encapsulation phase, and the carrier phase is maintained at the same time for providing higher transdermal delivery.

Preferably, the active ingredient is palmitoyl-pentapeptide-3.

A second aspect of the presently claimed invention is to provide a method for preparing a nanoemulsion.

According to an embodiment of the presently claimed invention, a method for preparing a nanoemulsion comprises: mixing the oil, the surfactant, the ethanol, and the active ingredient to form a first mixture; adding water into the first mixture dropwisely to from a second mixture; and stirring the second mixture or homogenizing the second mixture to form the nanoemulsion.

Preferably, the active ingredient is Schisandrin.

According to another embodiment of the presently claimed invention, a method for preparing a nanoemulsion comprises: mixing the oil, the surfactant, the ethanol, and the penetration enhancer to form a first mixture; mixing the active ingredient and the water to form a second mixture; adding the second mixture into the first mixture dropwisely to from a third mixture; stifling the third mixture to form the nanoemulsion.

Preferably, the active ingredient is an epidermal growth factor.

According to a further embodiment of the presently claimed invention, a method for preparing a nanoemulsion comprises: mixing the active ingredient, the oil, the surfactant, and the penetration enhancer to form a first mixture; adding water into the first mixture dropwisely to from a second mixture; and stirring the second mixture or homogenizing the second mixture to form the nanoemulsion.

Preferably, the active ingredient is palmitoyl-pentapeptide-3.

The present chemical formulation and method provide nanoemulsion having desirable particle size (below 100 nm) for efficient transdermal delivery. Accordingly, the nanoemulsion of the present invention is smaller than the conventional lipid vesicle having around 500 nm in size. In addition, the chemical formulation of the present invention doesn't involve any organic solvent which is harmful to human skin, and the corresponding fabrication method is simple.

BRIEF DESCRIPTION OF THE DRAWINGS

Embodiments of the present invention are described in more detail hereinafter with reference to the drawings, in which.

DETAILED DESCRIPTION OF PREFERRED EMBODIMENTS

In the following description, chemical formulations for preparing a nanoemulsion, and methods preparing the nanoemulsion for efficient transdermal delivery are set forth as preferred examples. It will be apparent to those skilled in the art that modifications, including additions and/or substitutions, may be made without departing from the scope and spirit of the invention. Specific details may be omitted so as not to obscure the invention; however, the disclosure is written to enable one skilled in the art to practice the teachings herein without undue experimentation.

EXAMPLE 1

A. Nanomization of Schisandrin B (Sch B)

A.1 Preparation of Sch B-nanoemulsion

Figure 1:
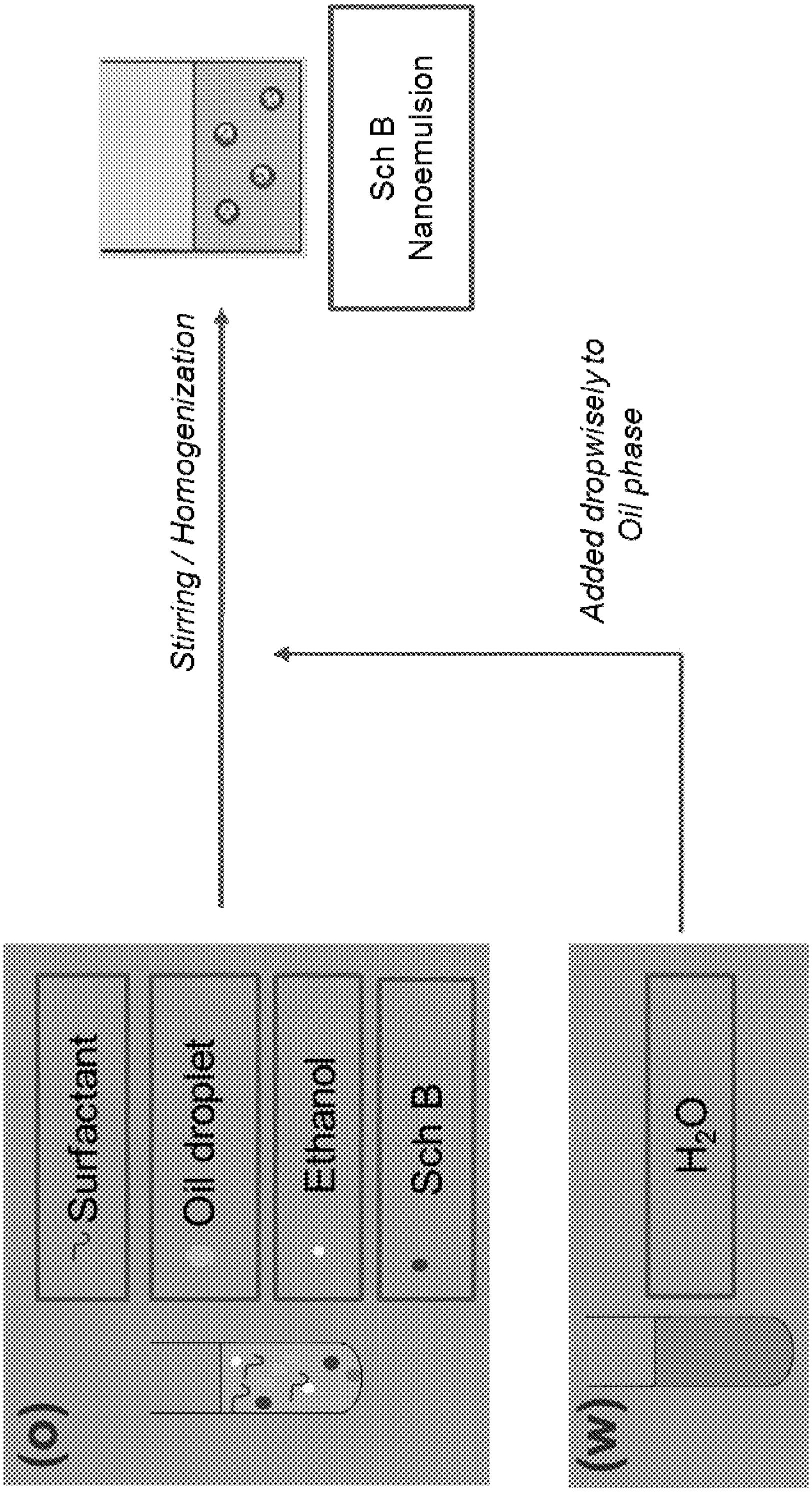
FIG. 1 is a schematic diagram of the nanomization preparation of Sch B according to an embodiment of the presently claimed invention.

The defined amount of Sch B, oil and surfactant were firstly mixed together with ethanol. The mixture was then sonicated for 10 minutes in sonication bath to obtain a clear homogenous solution. Then, the required amount of water was added dropwisely under magnetic stirring (1000-2000 rpm) or homogenization (5000-20000 rpm) to form nanoemulsion. Resulting nanoemulsion was further stirred for a define time (2-20 mins). The preparation strategy of nanoemulsion is illustrated in FIG. 1. The nanoemulsion was stored at room temperature for subsequent uses.

The nanoemulsion system consisted of water, ethanol, oil and surfactant. The ratio of water to ethanol plus oil and surfactant is in a critical ratio of 27:73. The ratio of ethanol to oil to surfactant is about 1:1:2. The oil which may be used in the nanoemulsion include, and are preferably chosen from the group formed by: (1) esters of polyols and of fatty acids, for example isopropyl myristate, caprylocaproyl polyoxylglycerides or ethyl oleate; (2) animal and vegetable fats and oils, which containing saturated alky chain lengths of around 10 carbons to 12 carbons attached to a polar head group, such as oleic acid, lauric acid or linoleic acid; (3) natural or synthetic essential oils, for example limonene or menthol. The amount of oil preferably ranges from 15 to 16% by weight with respect to the total weight of the nanoemulsion. The surfactants are preferably chosen from non-ionic surfactant, for example span 80, capryol 90, tween 20 or tween 80. The use of surfactants preferably ranges from 37 to 39% by weight. Ethanol and water are present in the nanoemulsion preferably ranges from 17 to 18% by weight and 26 to 27% by weight, respectively. The active ingredient to be loaded in the nanoemulsion system can be dibenzocyclooctadiene lignans and their derivatives, for example schisandrin A, schisandrin B, schisandrin C, gomisin A or gomisin J. The preferable percentage range of the active ingredient is 0.15 to 3.6%. The percentage range of each of the components and processing parameters in the nanoemulsion are shown in Table 1.

TABLE 1

The compositions percentage range of Sch B-nanoemulsion

| Chemical type | Oil % | Surfactant % | Ethanol % | Water % | Sch B % | Speed (rpm) | Time (min) |
|---|---|---|---|---|---|---|---|
| Composition | 15-16 | 37-39 | 17-18 | 26-27 | 0.15-3.6 | 1000-2000 (Magnetic Stirring) or 5000-20000 (Homogenization) | 2-20 |
| Ingredient | Isopropyl myristate | Tween 80 | Ethanol | Water | Sch B | | |

An example of compositions for preparation of Sch B-nanoemulsion is shown in Table 2.

TABLE 2

An example of compositions in Sch B-nanoemulsion

| Chemical type | Oil % | Surfactant % | Ethanol % | Water % | Sch B % | Speed (rpm) | Time (min) |
|---|---|---|---|---|---|---|---|
| Composition | 15.8 | 38.4 | 17.7 | 26.6 | 1.5 | 1000 | 20 |
| Ingredient | Isopropyl myristate | Tween 80 | Ethanol | Water | Sch B | (Magnetic Stirring) | |

A.2 Optimization of Sch B-nanoemulsion

In order to enhance the skin penetration of nanoemulsion, the effect of homogenization speed, homogenization time and the method of homogenization or stirring were optimized and selected based on particle size. The compositions of Sch B-nanoemulsion in these studies are listed in Table 2.

Figure 2:
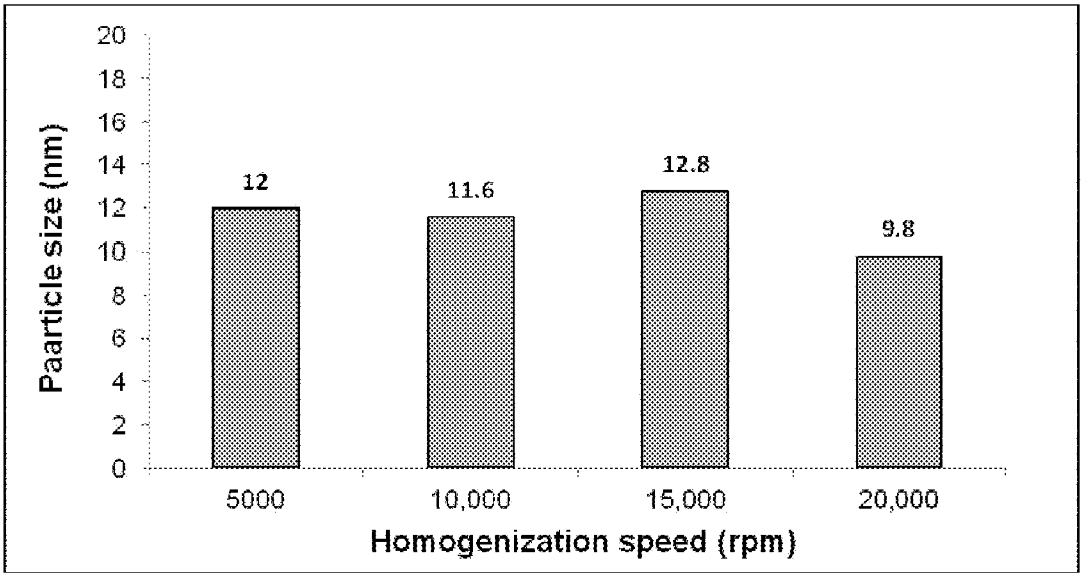
FIG. 2 is a graph showing the effect of homogenization speed on the particle size with homogenization time at 20 minutes in Sch B (1.5%) nanoemulsion formulations according to an embodiment of the presently claimed invention.

Sch B-nanoemulsion was prepared with different homogenization speed (5000, 10000, 15000 and 20000 rpm) and the homogenization time was held at 20 minutes. The Sch B concentration in the nanoemulsions was 1.5%. The results—are shown in FIG. 2. The results indicate that particle sizes are smaller than 15 nm at all homogenization speeds. The smallest size of particles was found at homogenization speed of 20000 rpm at size of 9.8 nm. Therefore, 20000 rpm was selected.

Figure 3:
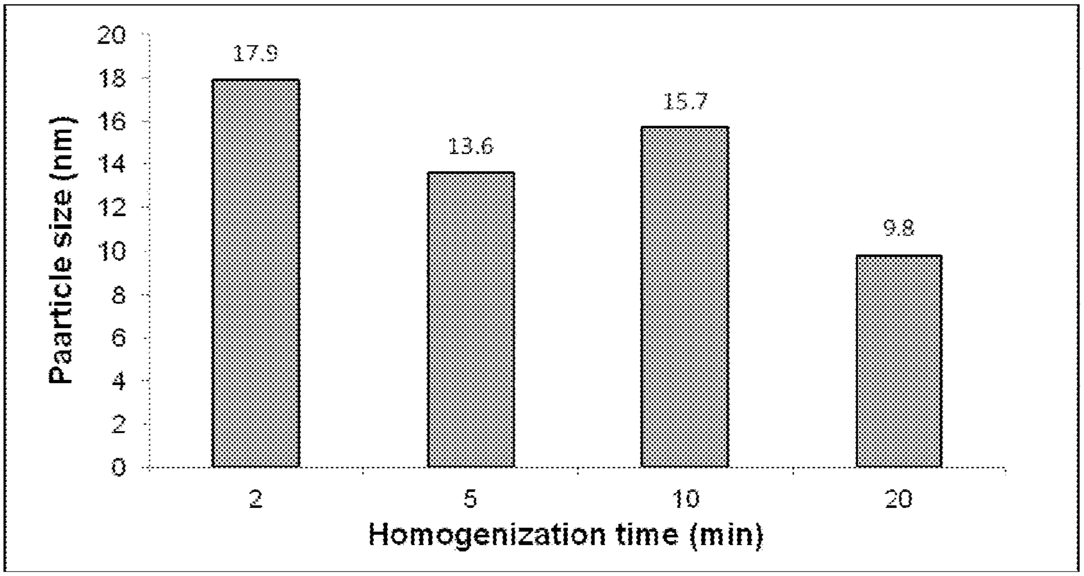
FIG. 3 is a graph showing The effect of homogenization time on the particle size with homogenization speed at 20000 rpm in Sch B (1.5%) nanoemulsion formulations according to an embodiment of the presently claimed invention.

The effect of homogenization time (2, 5, 10 and 20 minutes) on the size of particles is shown in FIG. 3. The test was performed at homogenization speed of 20000 rpm. The Sch B concentration in the nanoemulsions was 1.5%. The particle sizes at all different time are smaller than 20 nm. The smallest size of particles was found as 9.8 nm at 20 minutes of homogenization. 20 minutes was selected for homogenization.

Figure 4:
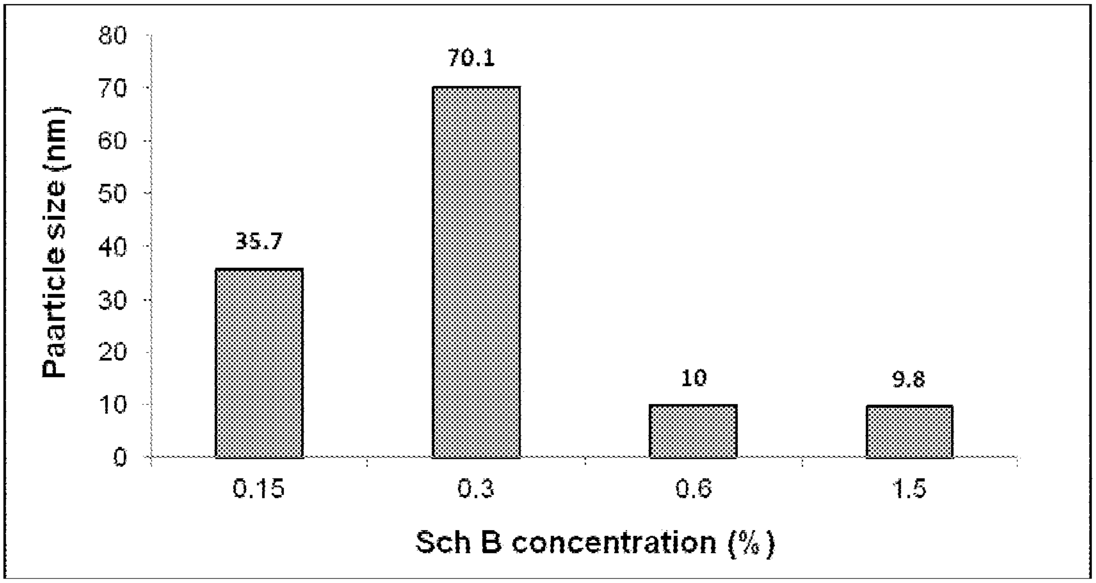
FIG. 4 is a graph showing the effect of Sch B concentration on the particle size with homogenization speed at 20000 rpm for 20 minutes in the nanoemulsion formulations according to an embodiment of the presently claimed invention.

In addition, the effect of concentration of Sch B (0.15%, 0.3%, 0.6% and 1.5%) on particle size of nanoemulsion was studied with homogenization speed set at 20000 rpm and homogenization time set at 20 minutes. Refer to FIG. 4, it was found that particle size decreased when wt % of Sch B increased. Sch B at 0.15% to 1.5% could produce similar small particles, which were under 80 nm. Therefore, this study demonstrated that Sch B concentration for nanoemulsion preparation can be applied at the range of 0.15% to 1.5%.

Figure 5:
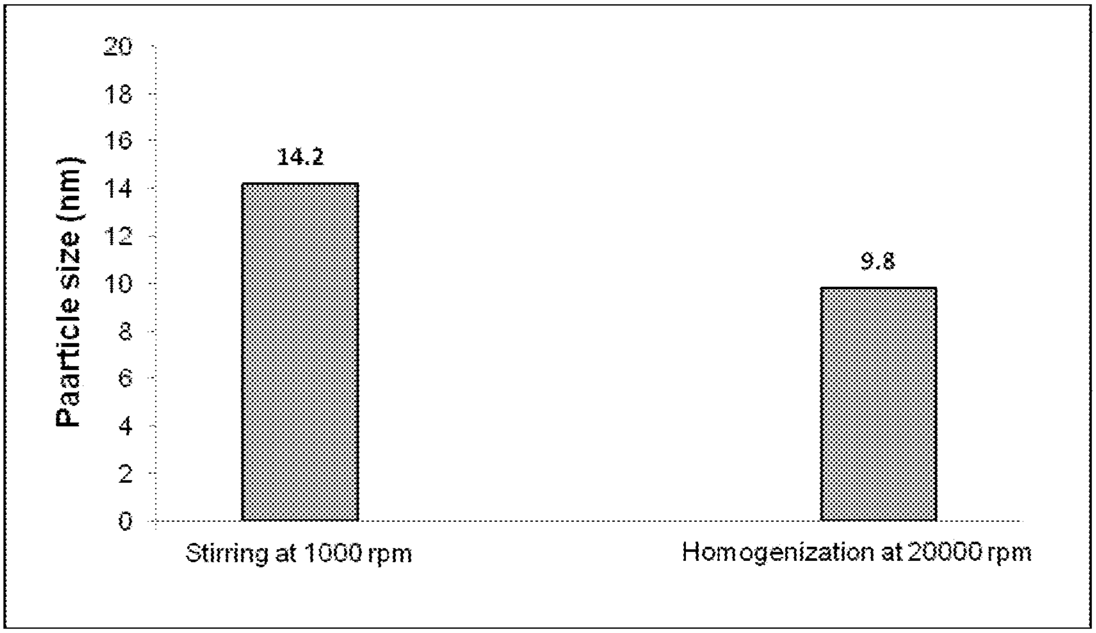
FIG. 5 is a graph showing a comparison on different methods for formation of particles in 1.5% Sch B-nanoemulsion according to an embodiment of the presently claimed invention.

The result comparison of the particle size produced by homogenization or stirring is shown in FIG. 5. The particles prepared by homogenization at 20000 rpm (9.8 nm) are comparable with that of stirring at 1000 rpm (14.2 nm). Both conditions were prepared with 20 minutes of mixing. The Sch B concentration in the nanoemulsions was 1.5%. Both homogenization and stirring could achieve particle size below 20 nm. Nevertheless, stifling is more preferred to produce active encapsulated nano-vesicles. In consideration of production and equipment cost in industrial scale, the Sch B-nanoemulsion prepared by stifling method was selected.

A.3 Preparation of Nanomzied Sch B Formulation Cream and Control Sample

The nanomzied Sch B formulation cream was prepared by mixing the Sch B-nanoemulsion with base cream in a specimen container. Sch B dissolved in ethanol/water mixture (WEtOH:Wwater=3:2) was then mixing with based cream in another specimen container as a control. Both mixtures were spun for 2 minutes to obtain homogenous cream. The volume ratio of nanomized or non-nanomized Sch B to base cream was 3:7.

A.4 In Vitro Skin Penetration Study

Vertical Franz-type diffusion cells were employed as in vitro skin penetration assay. The studies were performed in triplicate using pig ear skin samples with a total area of 6.25 $cm^2$. Before the experiments, the skin samples were cleaned with double deionized water, followed by 0.9% sodium chloride solution. The cleaned pig skin was fixed on the diffusion cells, with the orientation that the stratum corneum facing to the donor chamber. Active ingredient-loaded nanoemulsion formulation or control '(0.5 mL) was applied on the stratum corneum of the skin by the means of a syringe into the donor chamber. The donor compartment was then covered with parafilm to prevent evaporation. The dermal side of the skin was in contact with the receptor solution (0.9% sodium chloride), which was stirred continuously at 350 rpm. The experiment was run at temperature of 32.5° C. After the defined time period, 2 mL receptor solution was withdrawn through the sampling port of the receptor compartment. The remaining formulation on the skin was wiped off with a cotton wool, and the skin samples were taken out for active ingredient extraction. The amount of Sch B in the skin and receptor solution was determined by high performance liquid chromatography (HPLC).

A.5 Effect of Incubation Time in In Vitro Study on Skin Penetration

Figure 6:
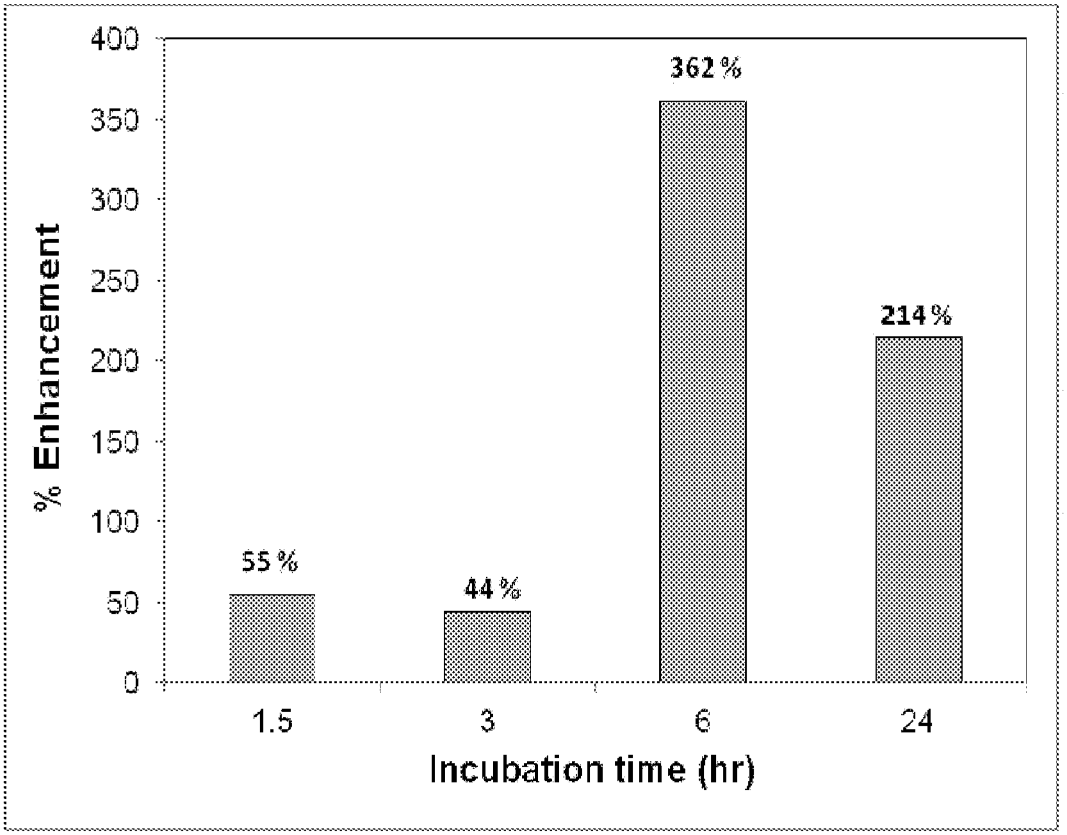
FIG. 6 is a graph showing the effect of incubation time of Sch B-nanoemulsion formulation in in vitro study on the enhancement of skin penetration according to an embodiment of the presently claimed invention.

Four different incubation time points (1.5 hours, 3 hours, 6 hours and 24 hours) in in vitro study on the percutaneous absorption of Sch B nanoemulsion formulation cream was investigated. FIG. 6 shows the effect of different incubation time points on the enhancement of skin penetration. Maximum skin penetration enhancement could be obtained when the formulation was incubated on skin for 6 hours, which shows 3.6 folds increment in skin penetration compared with control.

Figure 7:
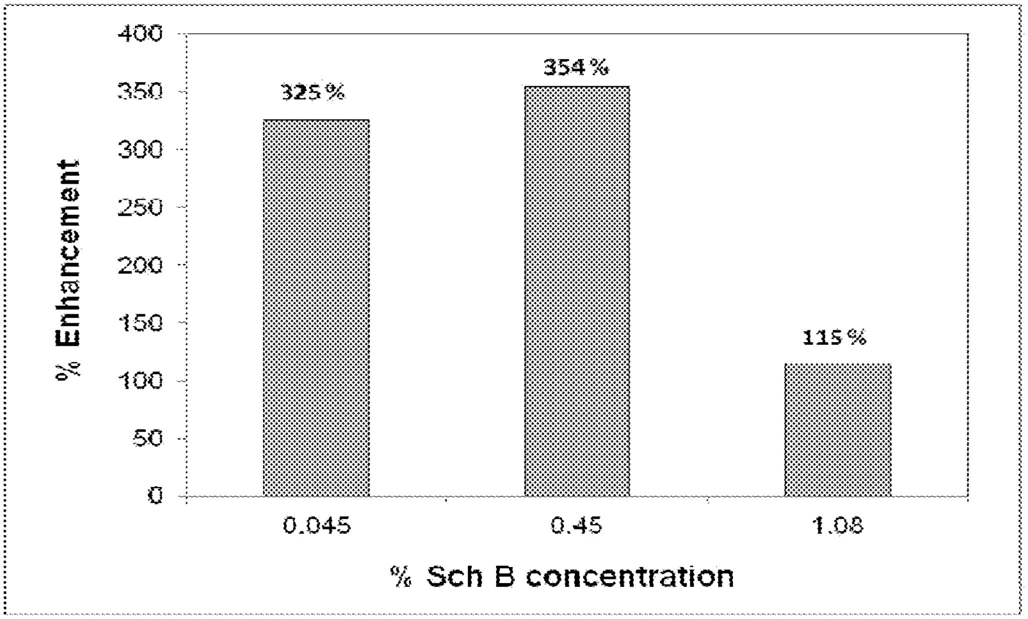
FIG. 7 is a graph showing the effect of Sch B concentration in nanomized Sch B formulation on the enhancement of skin penetration according to an embodiment of the presently claimed invention.

A.6 Effect of Sch B Concentration in Nanomized Sch B Formulation on Skin Penetration Three different concentrations of Sch B (0.045%, 0.45%, 1.08%) in nanomized Sch B formulation cream on the in vitro percutaneous absorption was tested. These creams were prepared from nanoemulsion containing 0.15%, 1.5% and 3.6% of Sch B, respectively. FIG. 7 shows the effect of Sch B concentration in Sch B nanoemulsion formulation on the enhancement of skin penetration. Skin penetration increased with Sch B concentration and maximum enhancement was found as 354% at concentration of 0.45%. Further increase of Sch B concentration from 0.45% to 1.08% in formulation reduces the skin penetration enhancement. Therefore, the optimum Sch B concentration in formulation cream is 0.45%.

The optimized Sch B nanoemulsion formulation (an working example)

A.7 Skin Penetration of Nanomized Sch B Formulation Cream Compared with Control

Figure 8:
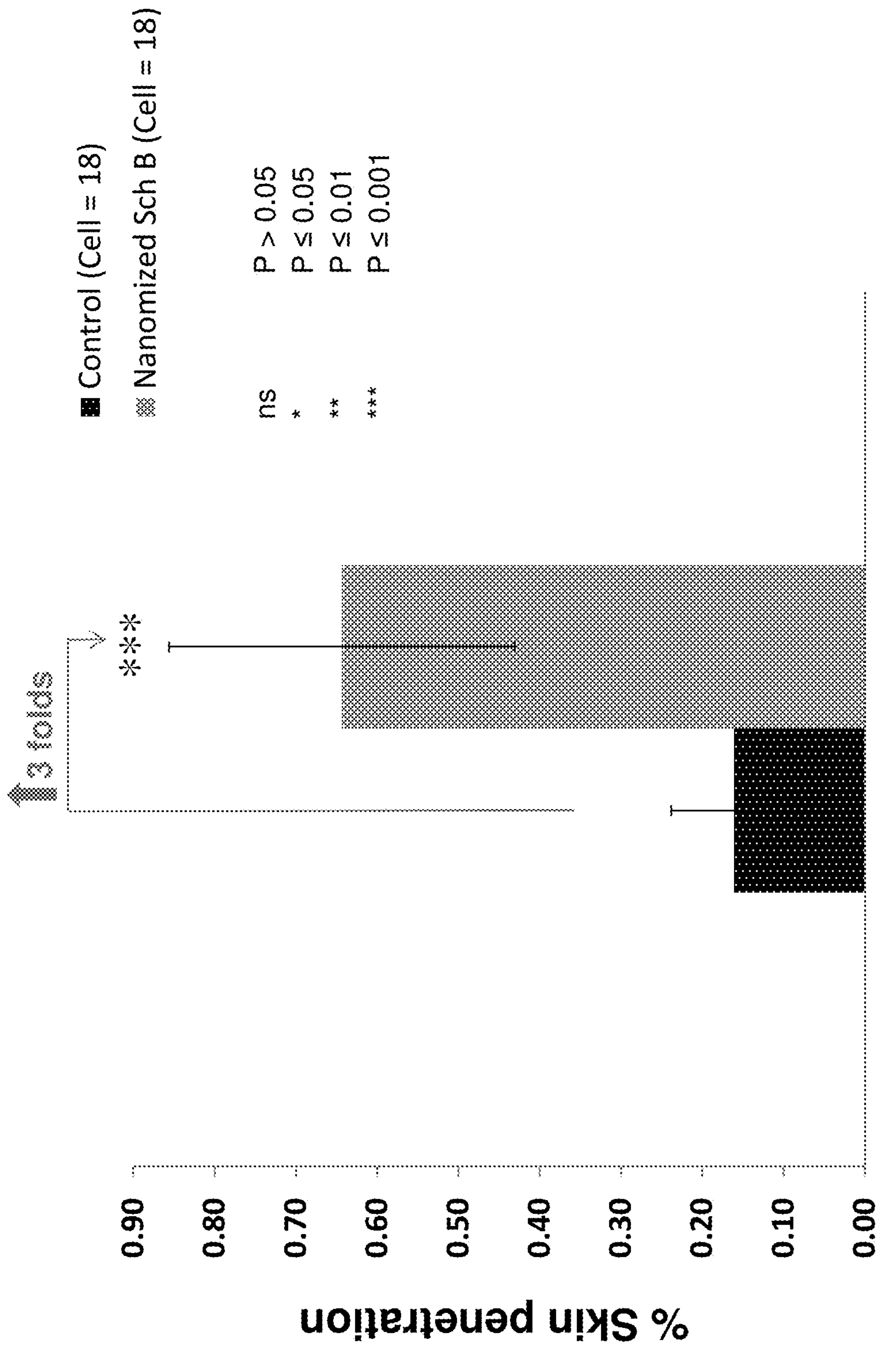
FIG. 8 is a graph showing Sch B skin penetrated percentage of nanomized Sch B formulation and control after 6 hours of diffusion cell experiment according to an embodiment of the presently claimed invention.

This is the skin penetration study of the optimized Sch B nanoemulsion stated in Table 2. FIG. 8 shows the percentage of nanomized Sch B formulation cream and control that penetrated to skin. The tested nanomized Sch B formulation cream and control contained 0.45% of Sch B. The nanomized Sch B formulation cream was prepared from 1.5% of Sch B nanoemulsion. The Sch B that penetrated into skin for the nanomzied Sch B formulation is 3 folds higher than that of control when tested for 6 hours. This result indicates that skin penetrating power of Sch B could be greatly enhanced through nanomization for transdermal delivery. The average particle size of the tested Sch B-nanoemulsion in this formulation was under 10 nm.

EXAMPLE 2

B. Nanomization of Palmitoyl-pentapeptide 3 (Pal-KTTKS)

B.1 Preparation of Pal-KTTKS-nanoemulsion

Figure 9:
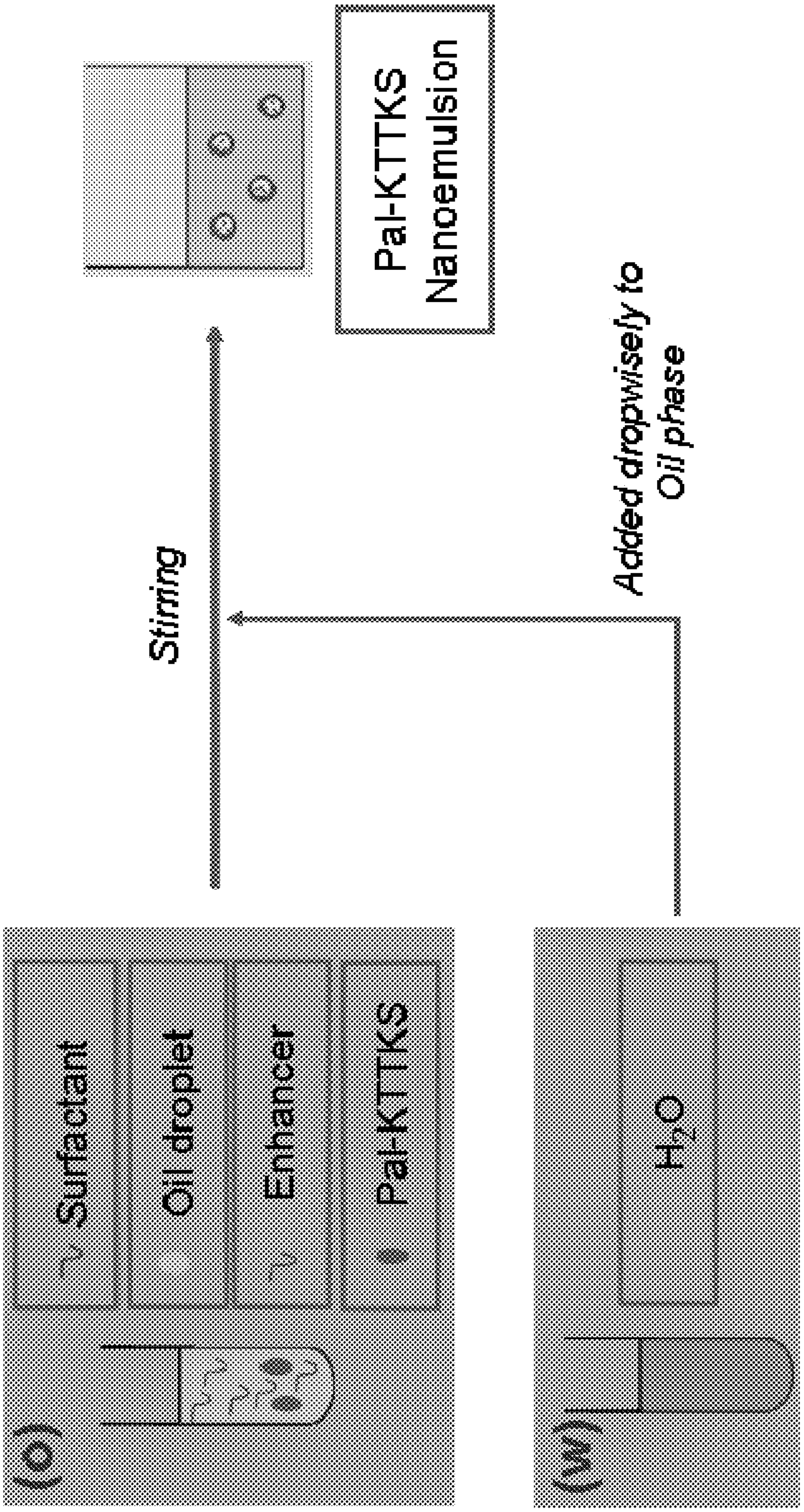
FIG. 9 is a schematic diagram of the nanomization preparation of Pal-KTTKS according to an embodiment of the presently claimed invention.

The required amount of Pal-KTTKS, surfactant, oil and enhancer were weighted with a pre-determined weight ratio in a 20 ml vial. The mixture was then sonicated for 30 seconds. Double deionized water was then added to the mixture dropwisely under magnetic stifling (500-1500 rpm) or homogenization (8000-20000 rpm). The resulting nanoemulsion was kept stirring for the defined time (1-10 mins) to reach equilibrium state (FIG. 9). The nanoemulsion was stored at room temperature for subsequent uses.

The Pal-KTTKS-nanoemulsion system consisted of water, oil phase, surfactant and penetration enhancer, wherein the water content is up to 90% or equal to 70% by weight and the weight ratio of oil:surfactant is in a critical ratio of 1:9. The oil phases which may be used in the nanoemulsion include, and are preferably chosen from the group formed by: (1) esters of polyols and of fatty acids, for example isopropyl myristate, caprylocaproyl polyoxylglycerides or ethyl oleate; (2) animal and vegetable fats and oils, which containing saturated alky chain lengths of around 10 carbons to 12 carbons attached to a polar head group, such as oleic acid, lauric acid or linoleic acid; (3) natural or synthetic essential oils, for example limonene or menthol; (4) lower C1-C8 glycols, such as glycerol, -capryol 90 or polyethylene glycols. The amount of oil preferably ranges from 1 to 3% by weight with respect to the total weight of the nanoemulsion. The surfactants are preferably chosen from non-ionic surfactant, for example, span 80, Labrasol, tween 20 or tween 80. The use of surfactants preferably ranges from 9 to 27% by weight. In addition, penetration enhancer, which may be used in the nanoemulsion include, and are preferably chosen from the group formed by: (1) terpene, for example carvone, geraniol or menthol; (2) Phospholipids, for example phosphatidylcholine; (3) urea. The use of penetration enhancers preferably ranges from 0.5 to 4% by weight. The active ingredient to be loaded in the nanoemulsion system can be palmitoyl peptides, for example palmitoyl dipeptide 6, palmitoyl tripeptide 5, palmitoyl tetrapeptide 3, palmitoyl pentapeptide 3 or palmitoyl hexapeptide. The preferable percentage range of the active ingredient is 0.05 to 6.7%. The percentage range of each of the components and processing parameter in the nanoemulsion are shown in Table 3.

TABLE 3

The compositions percentage range of Pal-KTTKS-nanoemulsion

| Chemical type | Oil % | Surfactant % | Water % | Pal-KTTKS % | Enhancer % | Speed (rpm) | Time (min) |
|---|---|---|---|---|---|---|---|
| Composition | 1-3 | 9-27 | 70-90 | 0.05-6.7 | 0.5-4 | 500-1500 | 1-10 |
| Ingredient | Capryol 90 | Tween 20 | Water | Pal-KTTKS | Phospholipid | (Magnetic Stirring) or 8000-20000 (Homogenization) | |

An example of compositions for preparation of Pal-KTTKS-nanoemulsion is shown in Table 4.

TABLE 4

An example of the compositions in Pal-KTTKS-nanoemulsion

| Chemical type | Oil % | Surfactant % | Water % | Pal-KTTKS % | Enhancer % | Speed (rpm) | Time (min) |
|---|---|---|---|---|---|---|---|
| Composition | 1 | 9 | 89 | 0.67 | 0.5 | 1500 | 1 |
| Ingredient | Capryol 90 | Tween 20 | Water | Pal-KTTKS | Phospholipid | (Magnetic Stirring) | |

B.2 Optimization of Pal-KTTKS-nanoemulsion

In order to enhance the skin penetration of nanoemulsion, the effect of homogenization speed and homogenization time were optimized and selected based on particle size. Furthermore, stifling method was also studied for the feasibility to produce nano-sized particles. The compositions of Pal-KTTKS-nanoemulsion in these studies are listed in Table 4.

Figure 10:
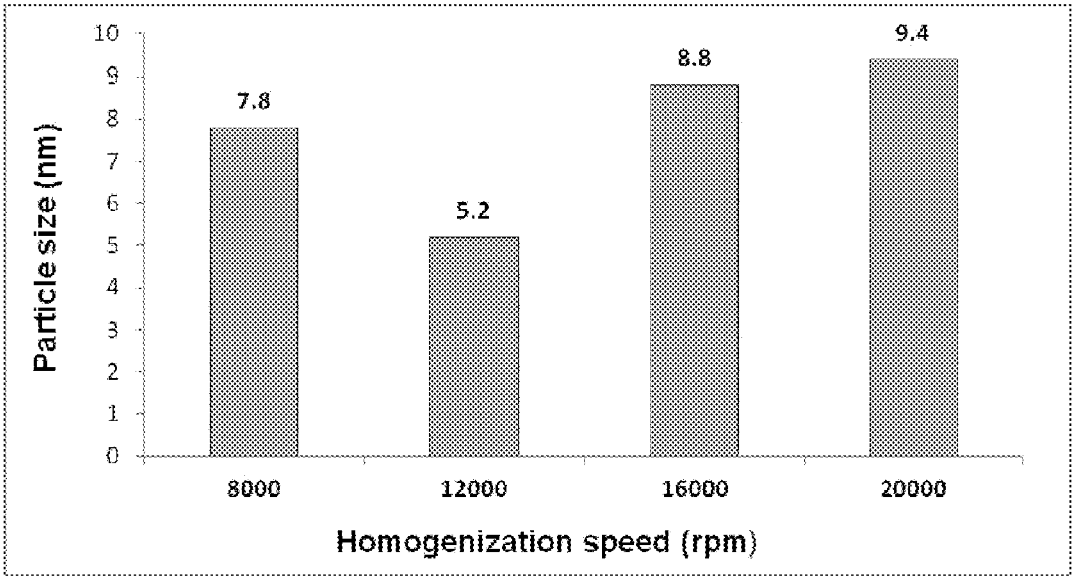
FIG. 10 is a graph showing the effect of homogenization speed on the particle size with homogenization time at 2 minutes in Pal-KTTKS (0.2%) nanoemulsion formulations according to an embodiment of the presently claimed invention.

The effect of homogenization speed on Pal-KTTKS particle size were studied at 8000, 12000, 16000 and 20000 rpm with homogenization time held at 2 minutes. The Pal-KTTKS concentration in the nanoemulsions was 0.2%. FIG. 10 indicates that the sizes of particles are all below 10 nm at different homogenization speeds. The smallest size of particles was found at homogenization speed at 12000 rpm with size 5.2 nm. Therefore, homogenization speed at 12000 rpm was selected.

Figure 11:
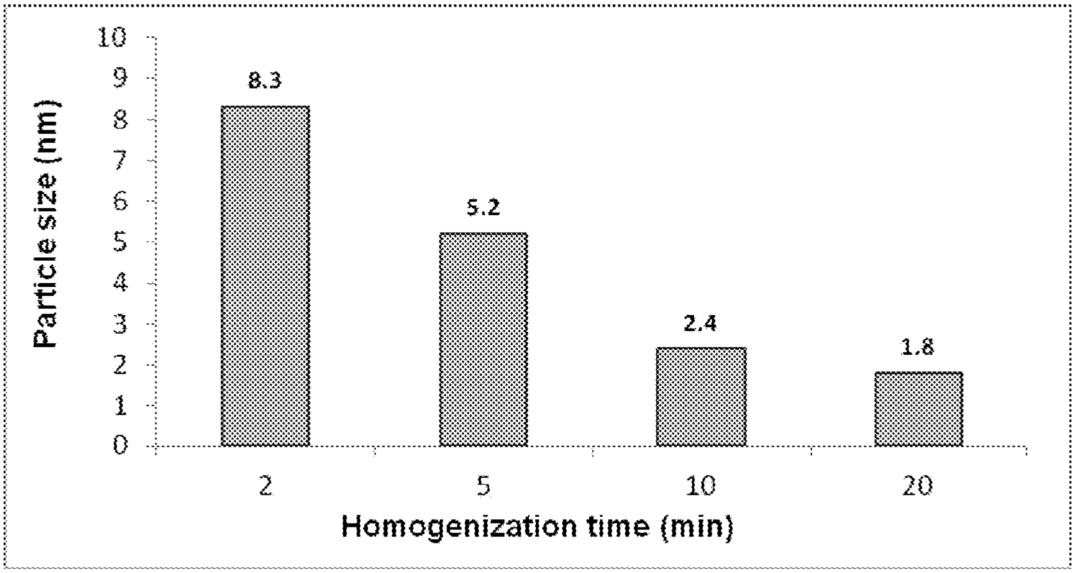
FIG. 11 is a graph showing the effect of homogenization time on the particle size with homogenization speed at 12000 rpm in Pal-KTTKS (0.2%) nanoemulsion formulations according to an embodiment of the presently claimed invention.

The effect of homogenization time on the size of particles was studied at 2, 5, 10 and 20 minutes with the homogenization speed held at 12000 rpm. The Pal-KTTKS concentration in the nanoemulsions was 0.2%. The results are shown in FIG. 11. It was found that all particles are below 10 nm at different homogenization time. The smallest size of particles was found as 1.8 nm at 20 minutes homogenization. This suggests that the condition of homogenization for 20 minutes should be selected.

Figure 12:
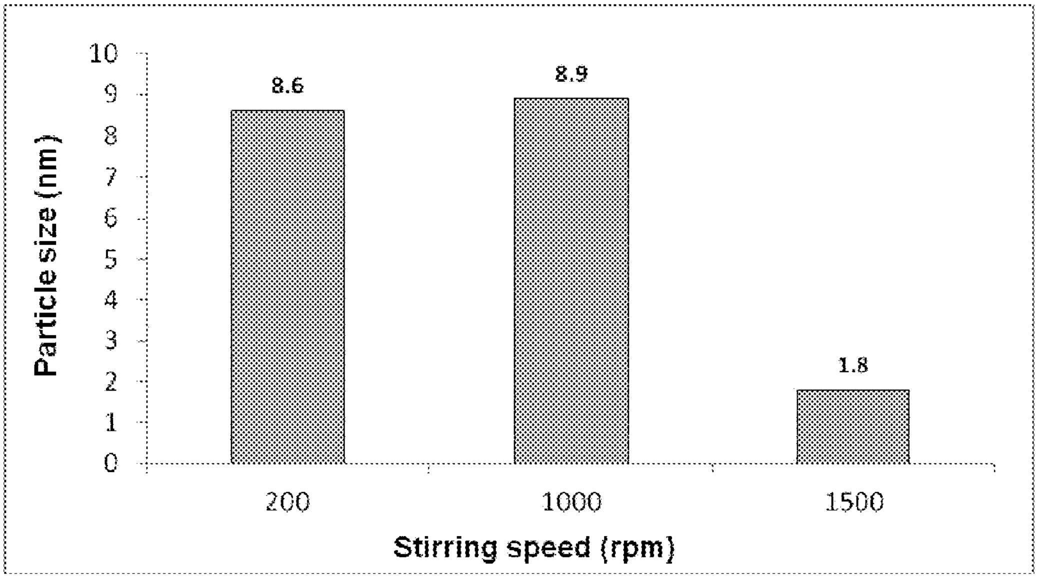
FIG. 12 is a graph showing the effect of stifling speed on the particle size with stifling time at 1 minute in Pal-KTTKS (0.2%) nanoemulsion formulations according to an embodiment of the presently claimed invention.

Besides homogenization, stifling can also be applied for producing the Pal-KTTKS-nanoemulsion. The effect of stifling speed for preparation of Pal-KTTKS-nanoemulsion was studied at 200, 1000 and 1500 rpm with the stirring time set at 1 minute. The Pal-KTTKS concentration in the nanoemulsions was 0.2%. The results (FIG. 12) indicate that particle sizes are smaller than 10 nm at all stifling speed. The smallest size of particles was found at stirring speed of 1500 rpm with size 1.8 nm. Therefore, stirring at 1500 rpm was selected.

Figure 13:
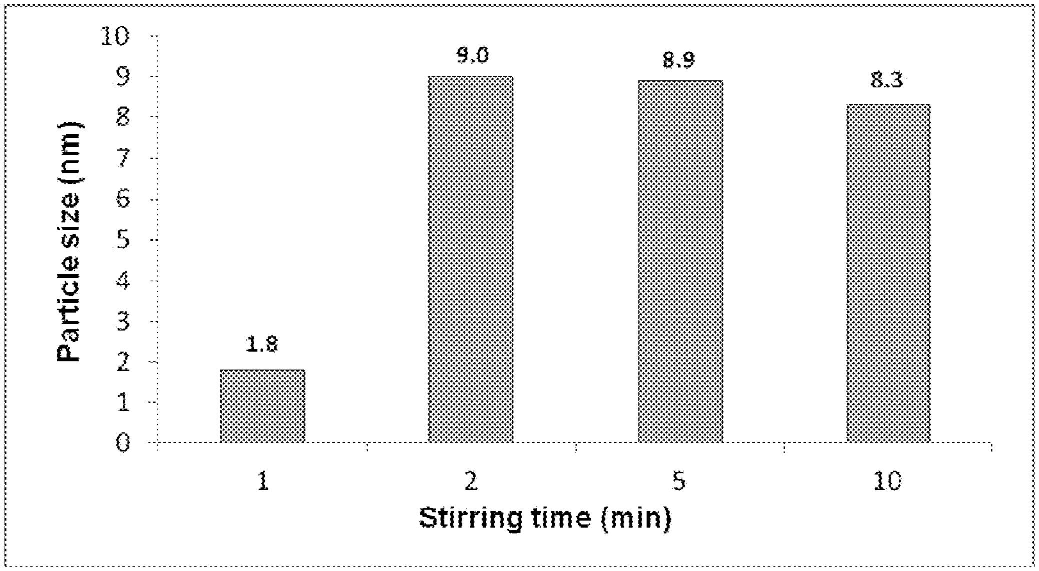
FIG. 13 is a graph showing the effect of stifling time on the particle size with stirring speed at 1500 rpm in Pal-KTTKS (0.2%) nanoemulsion formulations according to an embodiment of the presently claimed invention.
Figure 14:
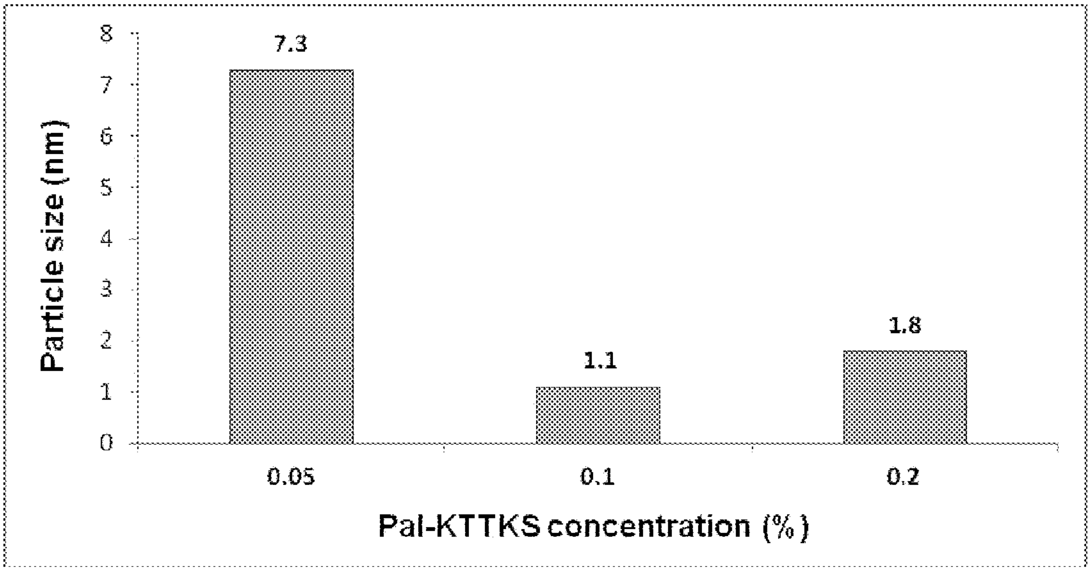
FIG. 14 is a graph showing The effect of Pal-KTTKS concentration on the particle size with stirring speed at 1500 rpm for 1 minute in the nanoemulsion formulations according to an embodiment of the presently claimed invention.

The effect of stirring time on the size of particles was examined at 1, 2, 5 and 10 minutes with the stifling speed held at 1500 rpm. The results are shown in FIG. 13. All particles are below 10 nm at different stifling time. The smallest size of particles was 1.8 nm after stirring for 1 minute. This suggests that the condition of stifling time for 1 minute should be selected. In the point of view on the cost of production and equipment in industrial scale, stirring method is more preferred to homogenization. Therefore, stirring at 1500 rpm for 1 minute was selected for preparation of Pal-KTTKS-nanoemulsion In addition, the effect of concentration of Pal-KTTKS (0.05%, 0.1% and 0.2%) on particle size of nanoemulsion was studied. The compositions and processing parameters of Pal-KTTKS-nanoemulsion in this study are listed in Table 4. FIG. 14 shows the results of effect of Pal-KTTKS concentration on particle size. The results indicate that the particle sizes are all less than 10 nm at different Pal-KTTKS concentration. Therefore, this study demonstrated that Pal-KTTKS concentration for nanoemulsion preparation can be applied at the range from 0.05% to 0.2%.

B.3 Preparation of Pal-KTTKS-nanoemulsion Formulation Cream and Control Sample

The Pal-KTTKS-nanoemulsion formulation cream was prepared by mixing the Pal-KTTKS-nanoemulsion with base cream in a specimen container. Pal-KTTKS dissolved in water was then mixing with base cream in another specimen container as a control. Both mixtures were spun for 2 minutes to obtain homogenous cream. The volume ratio of nanomized or non-nanomized Pal-KTTKS to base cream was 3:7.

B.4 In vitro Skin Penetration Study

The procedure is the same as described in 'In vitro skin penetration study' in Sch B. The amount of Pal-KTTKS in the skin and receptor solution was analyzed by LC/MS/MS.

B.5 Effect of Chemical Enhancers in Pal-KTTKS-nanoemulsion on Skin Penetration

Figure 15:
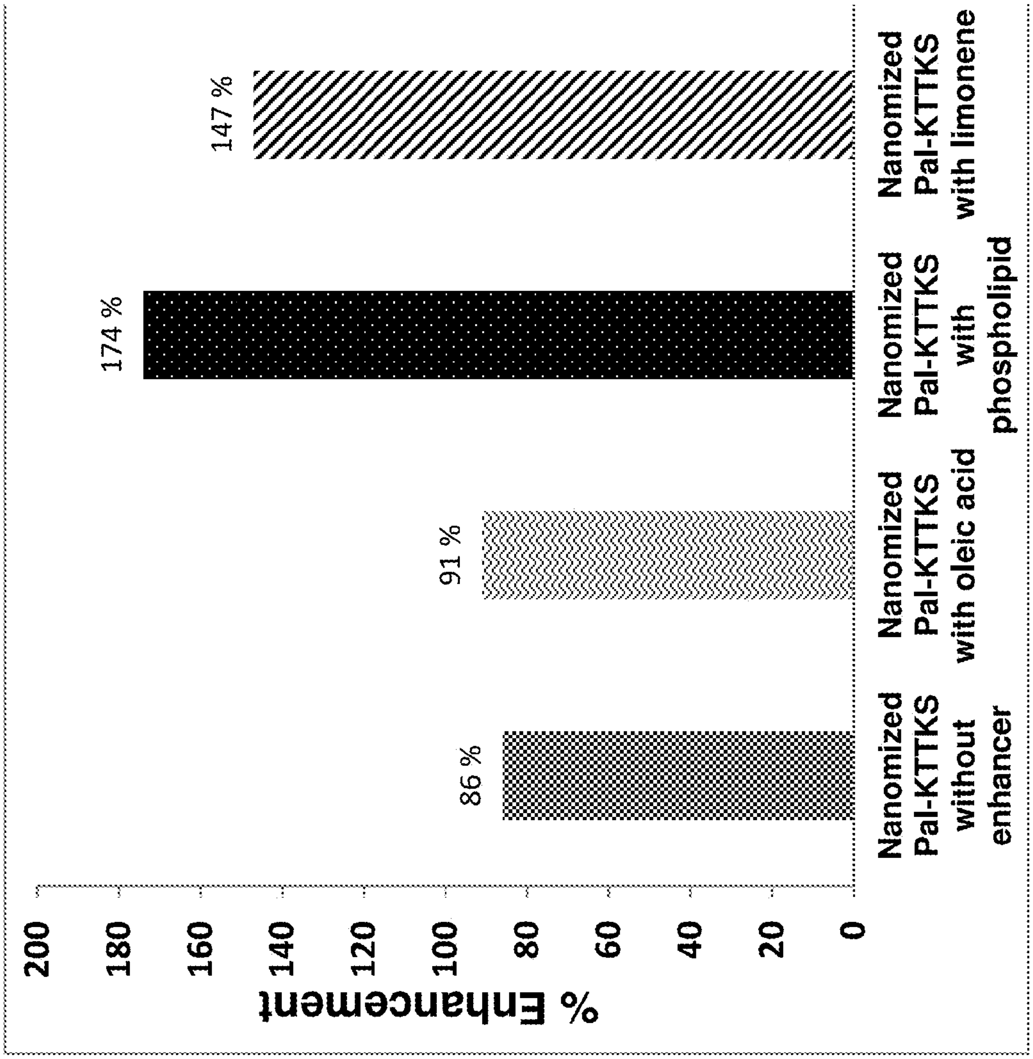
FIG. 15 is a graph showing in vitro study on the effect of 3 different chemical enhancers in the Pal-KTTKS-nanoemulsion on the skin penetration enhancement compared to control according to an embodiment of the presently claimed invention.

The effect of chemical enhancers on the skin penetration of Pal-KTTKS-nanoemulsion was studied with three different enhancers (limonene, phospholipid and oleic acid). FIG. 15 indicates that the highest enhancement of skin penetration could be obtained by addition of phospholipid to the formulation which shows 174% increment in skin penetration. Thus, phospholipid was chosen as the chemical enhancer in the Pal-KTTKS nanoemulsion.

Figure 16:
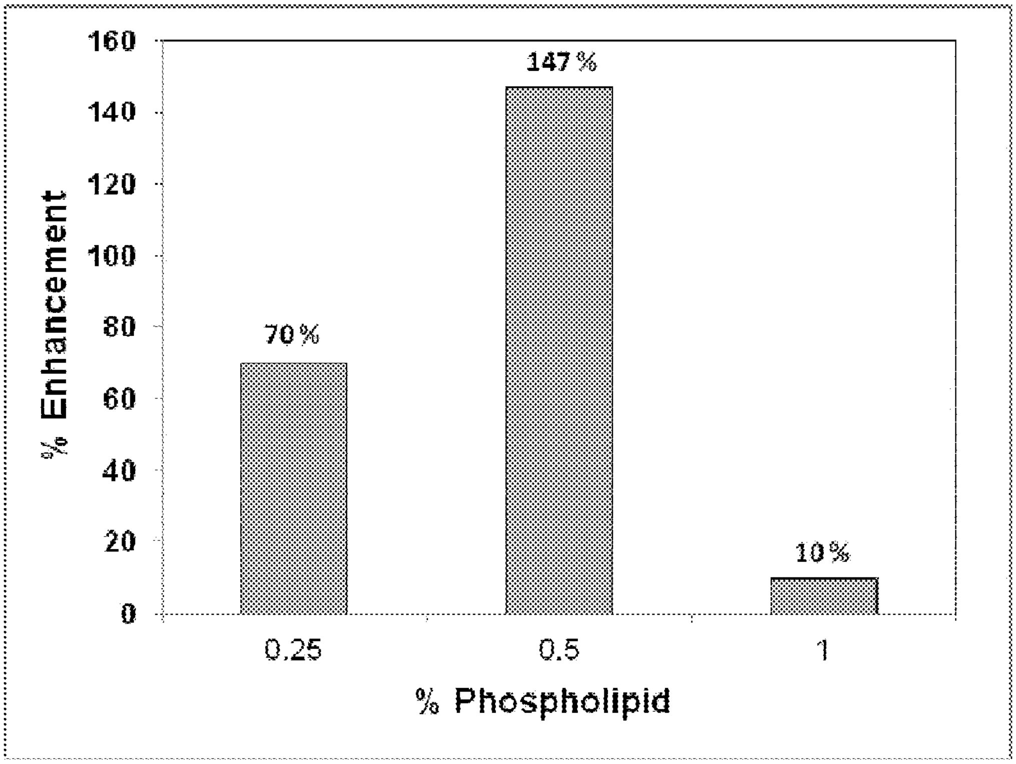
FIG. 16 is a graph showing the effect of phospholipid concentration in nanomized Pal-KTTKS formulation on the enhancement of skin penetration according to an embodiment of the presently claimed invention.

Three different concentrations of phospholipid (0.25%, 0.5% and 1%) on the in vitro percutaneous absorption of Pal-KTTKS-nanoemulsion were tested. FIG. 16 shows the effect of phospholipid concentration in Pal-KTTKS nanoemulsion on the enhancement of skin penetration. When 0.5% of phospholipid was added to the formulation, the highest increment in skin penetration with 147% could be achieved compared with control. The results suggested that 0.5% of phospholipid as the chemical enhancer should be used in the formulation.

B.6 Effect of Incubation Time in In Vitro Study on Skin Penetration

Figure 17:
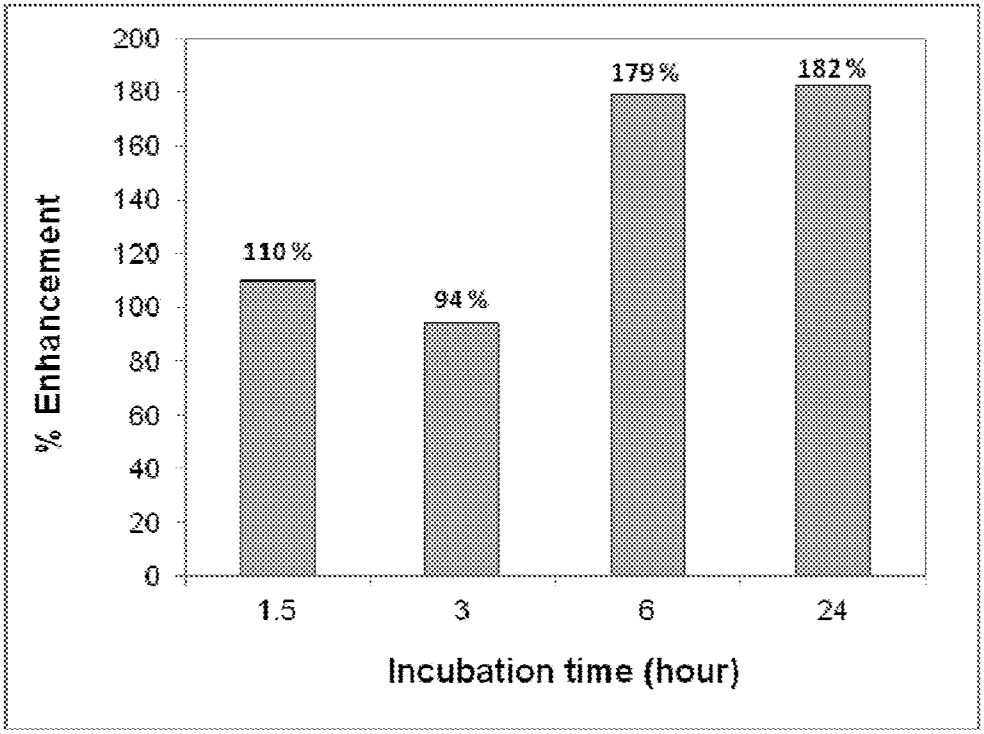
FIG. 17 is a graph showing the effect of incubation time of Pal-KTTKS-nanoemulsion formulation in in vitro study on the enhancement of skin penetration according to an embodiment of the presently claimed invention.

Four different incubation time points (1.5 hours, 3 hours, 6 hours and 24 hours) in in vitro study on the percutaneous absorption of Pal-KTTKS nanoemulsion formulation was investigated. FIG. 17 shows the effect of different incubation time points on the enhancement of skin penetration. It was found that a significant increase in skin penetration could be achieved for incubation time at 6 hours and 24 hours, which show 179% and 182% increment compared with control respectively. As the enhancement of skin penetration for 6 and 24 hours are comparable, a shorter time would be considered as the best incubation time.

Figure 18:
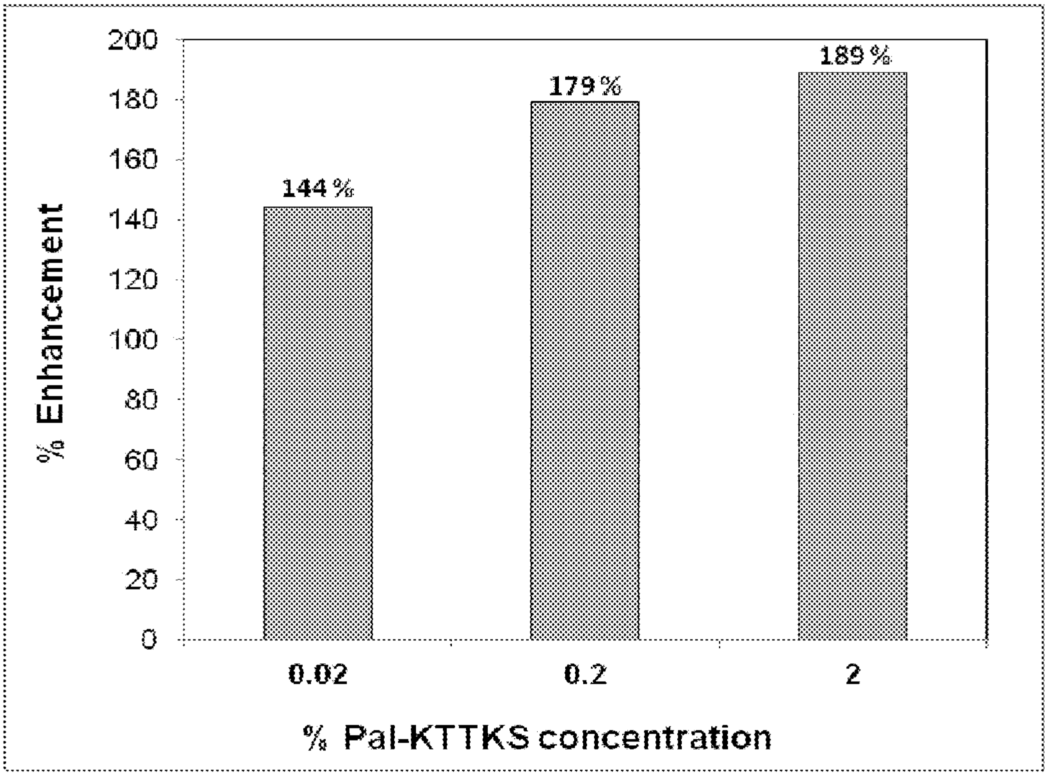
FIG. 18 is a graph showing the effect of Pal-KTTKS concentration in nanomized Pal-KTTKS formulation on the enhancement of skin penetration according to an embodiment of the presently claimed invention.

B.7 Effect of Concentration of Pal-KTTKS in Nanomized Pal-KTTKS Formulation Cream on Skin Penetration Three different concentrations of Pal-KTTKS (0.02%, 0.2%, 2%) in nanomized Pal-KTTKS formulation cream on the in vitro percutaneous absorption were tested. These creams were prepared from nanoemulsion containing 0.067%, 0.67% and 6.7%, respectively. FIG. 18 shows the effect of Pal-KTTKS concentration in Pal-KTTKS nanoemulsion formulation on the enhancement of skin penetration. The highest skin penetration enhancement could be obtained at Pal-KTTKS concentration of 2%. The range of Pal-KTTKS marketed cosmetic products is under 1%, therefore, 0.2% was chosen as the appropriate concentration.

The optimized Pal-KTTKS nanoemulsion formulation (an working example)

Figure 19:
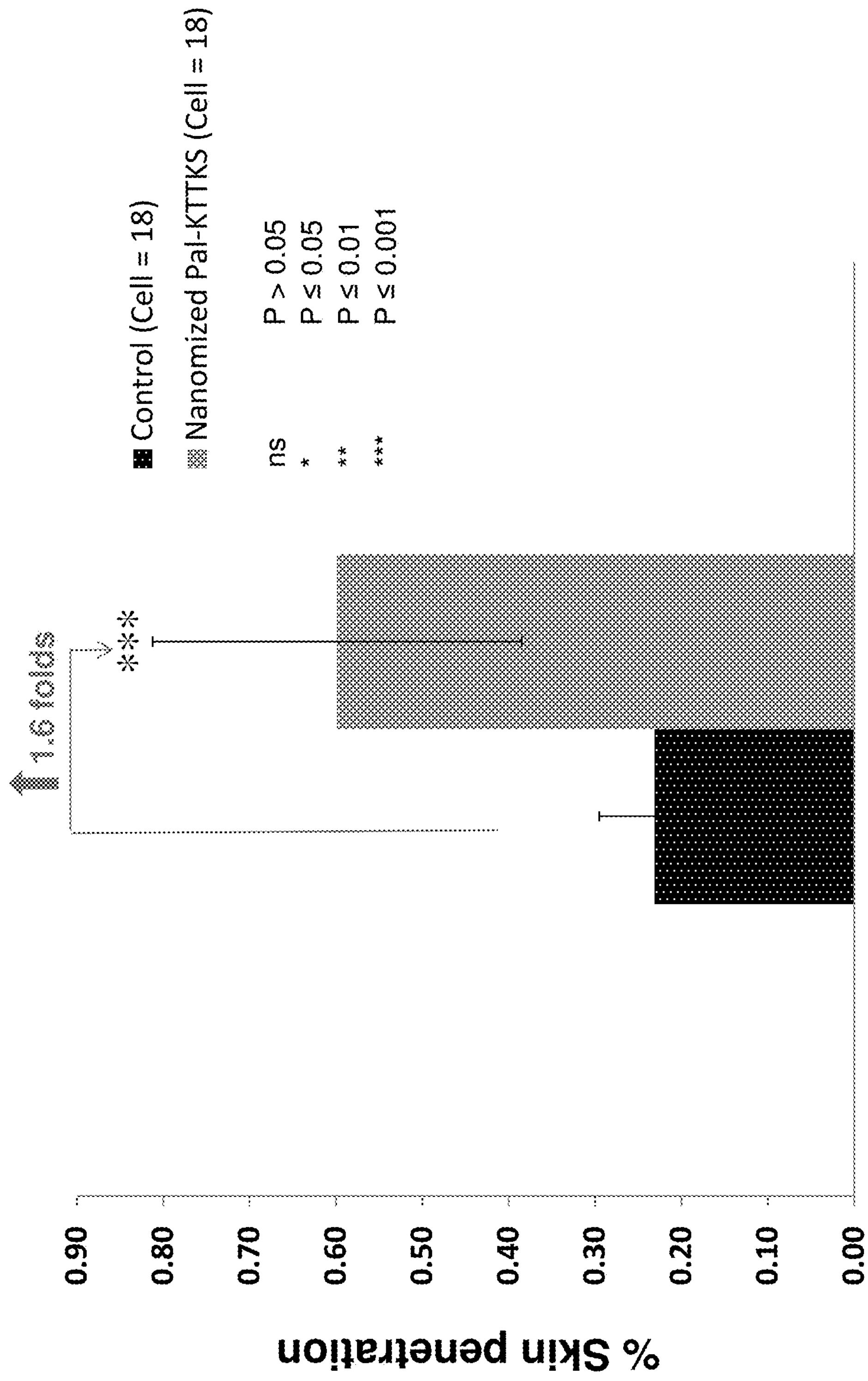
FIG. 19 is a graph showing percentage of Pal-KTTKS penetrated into skin in nanomized and control formulation after 6 hours of diffusion cell experiment according to an embodiment of the presently claimed invention.

B.8 Skin Penetration of Nanomized Pal-KTTKS Formulation Cream Compared with Control This is the skin penetration study of the optimized Pal-KTTKS nanoemulsion stated in Table 4. FIG. 19 shows the skin penetrated percentage of Pal-KTTKS in nanomized and control formulation. The tested nanomized Pal-KTTKS formulation cream and control contained 0.2% of Pal-KTTKS. The nanomized Pal-KTTKS formulation cream was prepared from 0.67% of Pal-KTTKS nanoemulsion. There is 1.6 fold increment in skin penetration of the Pal-KTTKS-nanomized formulation cream compared with control when tested for 6 hours. This result indicates Pal-KTTKS could be effectively penetrated to skin through this formulation. The average particle size of the tested Pal-KTTKS-nanoemulsion in this formulation was under 10 nm.

EXAMPLE 3

C. Nanomization of Epidermal Growth Factor (EGF)

C.1 Preparation of EGF-nanoemulsion

Figure 20:
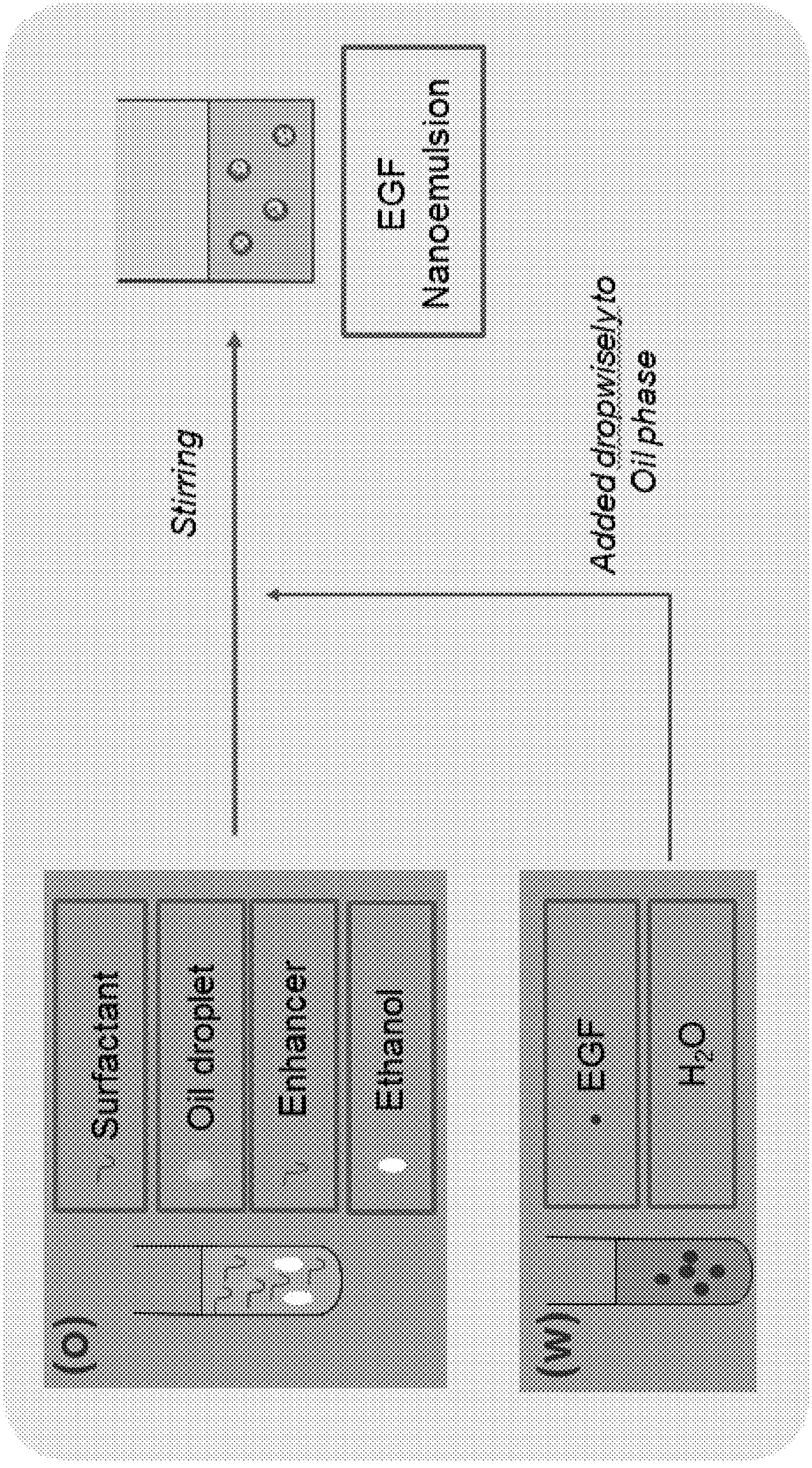
FIG. 20 is a schematic diagram of the nanomization preparation of EGF according to an embodiment of the presently claimed invention.

The defined amount of oil and surfactant were firstly mixed together with ethanol. Terpene was added as a skin penetration enhancer. The mixture was then sonicated for 10 minutes in sonication bath to obtain a clear homogenous solution. The required amount of water containing EGF was added dropwisely under magnetic stifling (1000-2000 rpm) to form nanoemulsion. Resulting nanoemulsion was further stirred for defined time (1-20 mins). The preparation strategy of nanoemulsion is illustrated in FIG. 20. The nanoemulsion was stored at room temperature for subsequent uses.

The EGF nanoemulsion system consisted of water, ethanol, oil, surfactant and penetration enhancer. The ratio of water to ethanol plus oil and surfactant is in a critical ratio of 22:78. The ratio of ethanol to oil to surfactant is about 1:1:2. The oil which may be used in the nanoemulsion include, and are preferably chosen from the group formed by: (1) esters of polyols and of fatty acids, for example isopropyl myristate, caprylocaproyl polyoxylglycerides or ethyl oleate; (2) animal and vegetable fats and oils, which containing saturated alky chain lengths of around 10 carbons to 12 carbons attached to a polar head group, such as oleic acid, lauric acid or linoleic acid; (3) natural or synthetic essential oils, for example limonene, or menthol. The amount of oil phase preferably ranges from 16 to 17% by weight with respect to the total weight of the nanoemulsion. The surfactants are preferably chosen from non-ionic surfactant, for example, span 80, capryol 90, tween 20 or tween 80. The use of surfactants preferably ranges from 39 to 42% by weight. Ethanol and water are present in the nanoemulsion preferably ranges from 18 to 19% by weight and 19 to 21% by weight, respectively. In addition, penetration enhancer, which may be used in the nanoemulsion include, and are preferably chosen from the group formed by: (1) terpene, for example carvone, geraniol or menthol; (2) Phospholipids, for example phosphatidylcholine; (3) urea. The use of penetration enhancers preferably ranges from 0.5 to 4% by weight. The active ingredient to be loaded in the nanoemulsion system can be water-soluble growth factors, for example epidermal growth factor, transforming growth factor beta, vascular endothelial growth factor, keratinocyte growth factor, interleukins or insulin-like growth factor 1. The preferable percentage range of the active ingredient is 0.0067-0.1333%. The percentage range of each of the components and processing parameters in the nanoemulsion are shown in Table 5.

TABLE 5

The compositions percentage range of EGF-nanoemulsion

| Ingredients | Oil phase % | Surfactant % | Ethanol % | Water % | EGF % | Terpene % | Speed (rpm) | Time (min) |
|---|---|---|---|---|---|---|---|---|
| Composition | 16-17 | 39-42 | 18-19 | 19-21 | 0.0067-0.1333 | 0.5-4 | 1000-2000 | 1-20 |
| Actives | Isopropyl myristate | Tween 80 | Ethanol | Water | EGF | Geraniol | (Magnetic Stirring) | |

An example of compositions and ingredients for preparation of the EGF nanoemulsion is shown in Table 6.

TABLE 6

An example of compositions in EGF-nanoemulsion

| Ingredients | Oil phase % | Surfactant % | Ethanol % | Water % | EGF % | Terpene % | Speed (rpm) | Time (min) |
|---|---|---|---|---|---|---|---|---|
| Composition | 17 | 42 | 19 | 21 | 0.067 | 1 | 1000 | 1 |
| Actives | Isopropyl myristate | Tween 80 | Ethanol | Water | EGF | Geraniol | (Magnetic Stirring) | |

C.2 Preparation of Nanomized EGF Formulation and Control Sample

The EGF-formulation was prepared by mixing the EGF-nanoemulsion with base cream in a specimen container. EGF dissolved in water was then mixing with based cream in another specimen container as a control. Both mixtures were spun for 2 minutes to obtain homogenous cream. The volume ratio of nanomized or non-nanomized EGF to base cream was 3:7.

C.3 In vitro Skin Penetration Study

The procedure is the same as described in 'In vitro skin penetration study' in Sch B. The amount of EGF in the skin and receptor solution was determined by ELISA.

Figure 21:
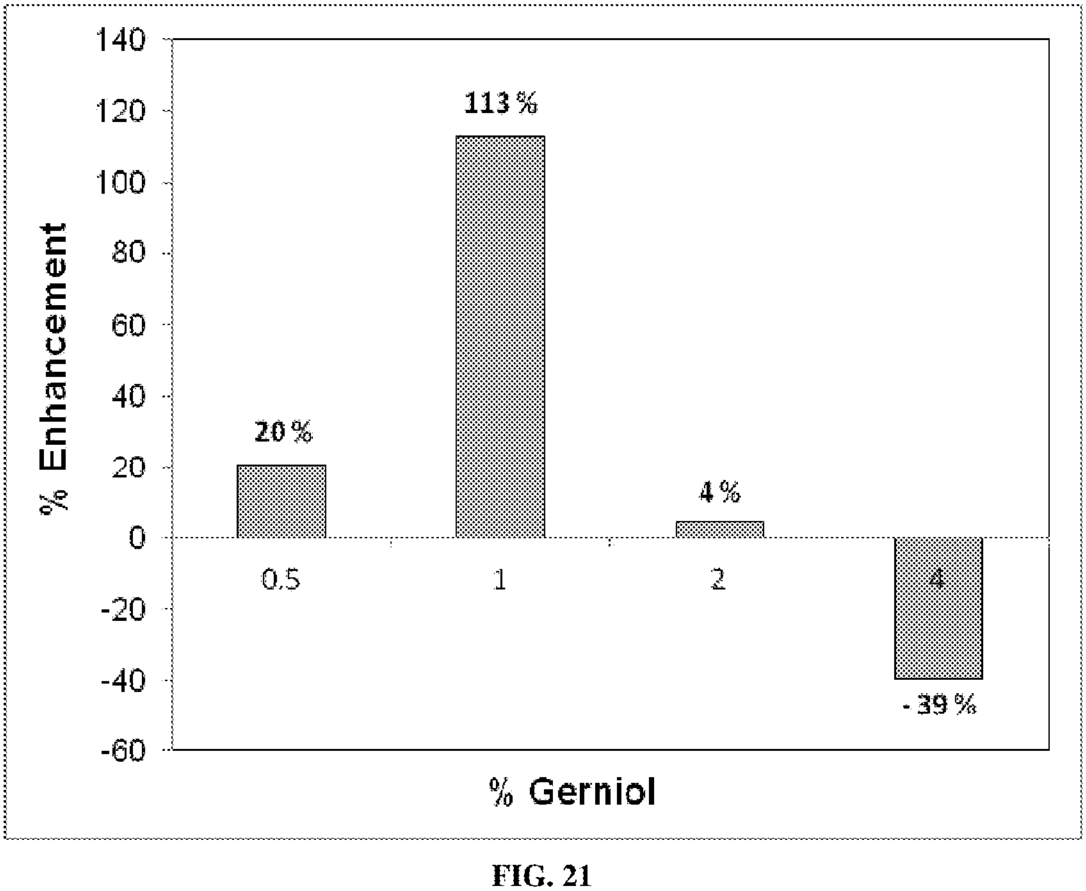
FIG. 21 is a graph showing the effect of geraniol concentration in nanomized EGF formulation on the enhancement of skin penetration according to an embodiment of the presently claimed invention.

C.4 Effect of Concentration of Terpene in Nanomized EGF Formulation on Skin Penetration The compositions of EGF-nanoemulsion in following studies are listed in Table 6. As the stratum corneum provides greatest resistance to percutaneous absorption, chemical enhancer such as terpene were added to achieve better skin penetration. In this study, the enhancing effect of different concentration of geraniol (0.5%, 1%, 2% and 4%) on the in vitro percutaneous absorption of nanomized EGF formulation was investigated. FIG. 21 shows the effect of geraniol concentration in nanomized EGF formulation on the enhancement of skin penetration. When 0.5% of geraniol was used, there is 20% increment in skin penetration compared with control. Further increase the concentration of geraniol to 1%, 113% increment in skin penetration was achieved. However, the increase of concentration of geraniol over 1% resulted in a significant reduction of skin penetration enhancement. Thus, it was suggested that 1% of geraniol as the chemical enhancer should be used in the formulation.

C.5 Effect of Incubation Time in In Vitro Study on Skin Penetration

Figure 22:
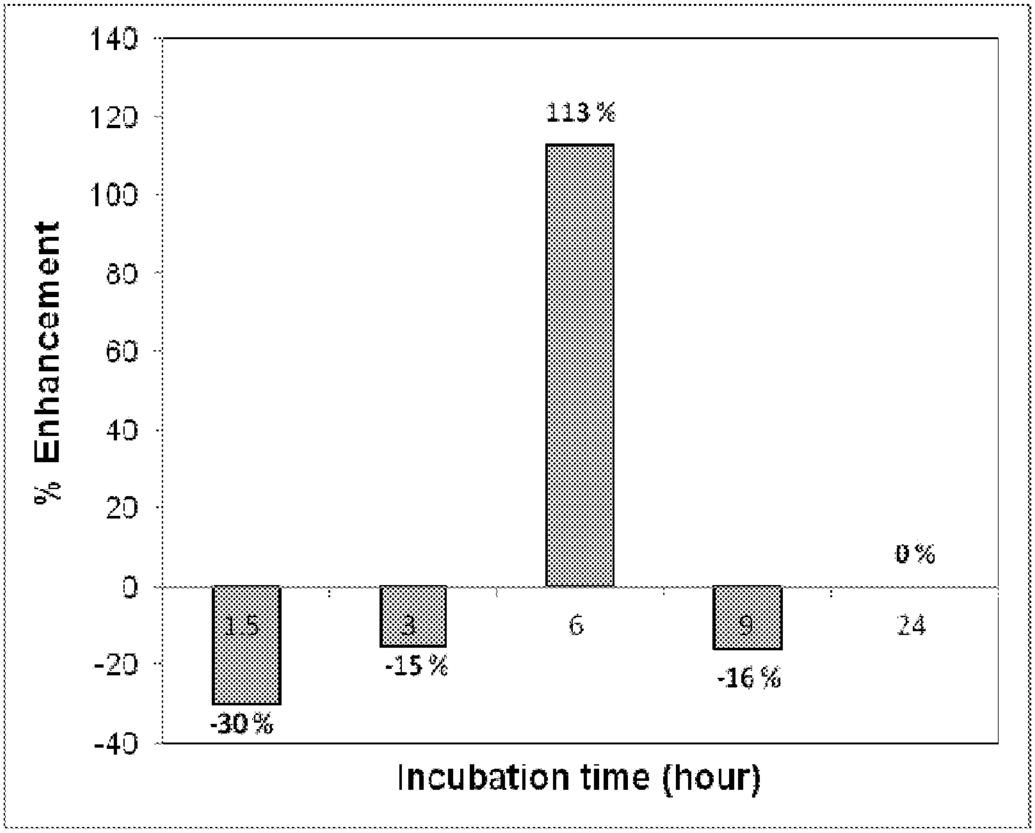
FIG. 22 is a graph showing the effect of incubation time EGF-nanoemulsion formulation in in vitro study on the enhancement of skin penetration according to an embodiment of the presently claimed invention.

Five different incubation time points (1.5 hours, 3 hours, 6 hours, 9 hours and 24 hours) in in vitro study on the percutaneous absorption of nanomized EGF formulation was investigated. FIG. 22 shows the effect of different incubation time points on the enhancement of skin penetration. All time points show no skin penetration enhancement except incubation time for 6 hours which has 113% increment in skin penetration compared with control.

Figure 23:
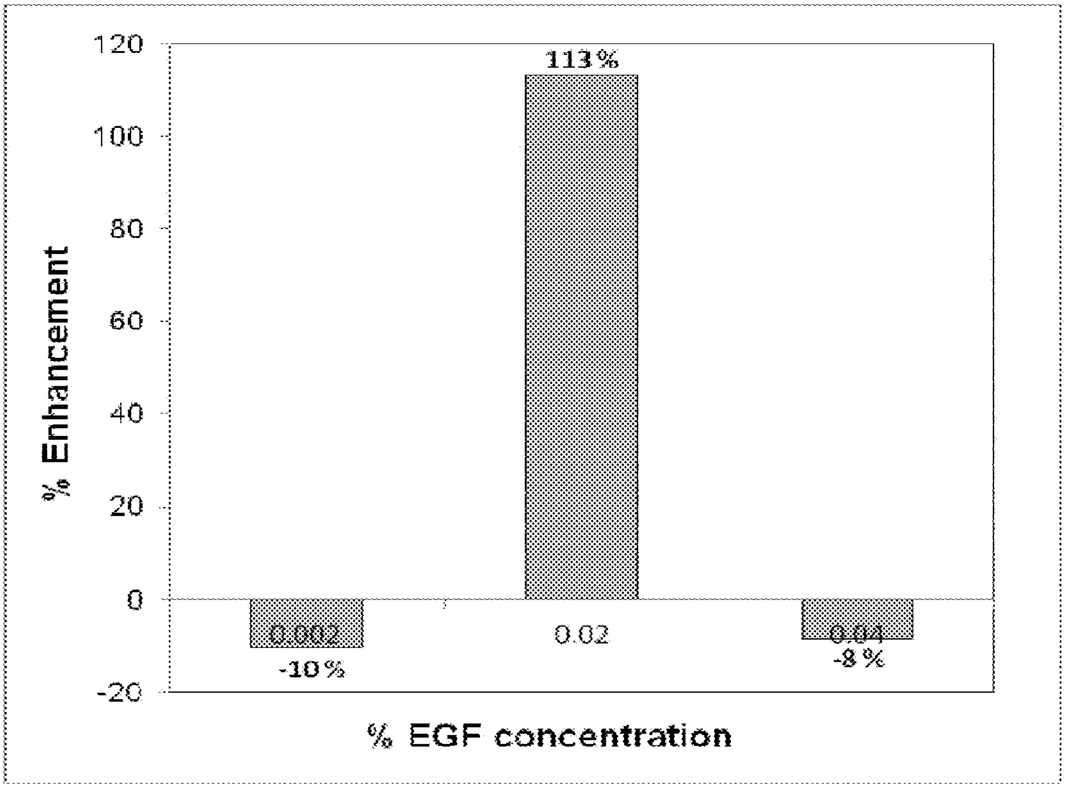
FIG. 23 is a graph showing the effect of EGF concentration in nanomized EGF formulation on the enhancement of skin penetration according to an embodiment of the presently claimed invention.

C.6 Effect of Concentration of EGF in Nanomized EGF Formulation Cream on Skin Penetration Three different concentration of EGF (0.002%, 0.02%, 0.04%) in nanomized EGF formulation cream on the in vitro percutaneous absorption was tested. These cream were prepared from nanoemulsion containing 0.0067%, 0.067% and 0.67% of EGF, respectively. FIG. 23 shows the effect of EGF concentration in nanomized EGF formulation on the enhancement of skin penetration. Concentration of EGF less or more than 0.02% shows no skin penetration enhancement. Thus, EGF with concentration of 0.02% should be chosen in the formulation.

C.7 Skin Penetration of Nanomized EGF Formulation Ccream Compared with Ccontrol

Figure 24:
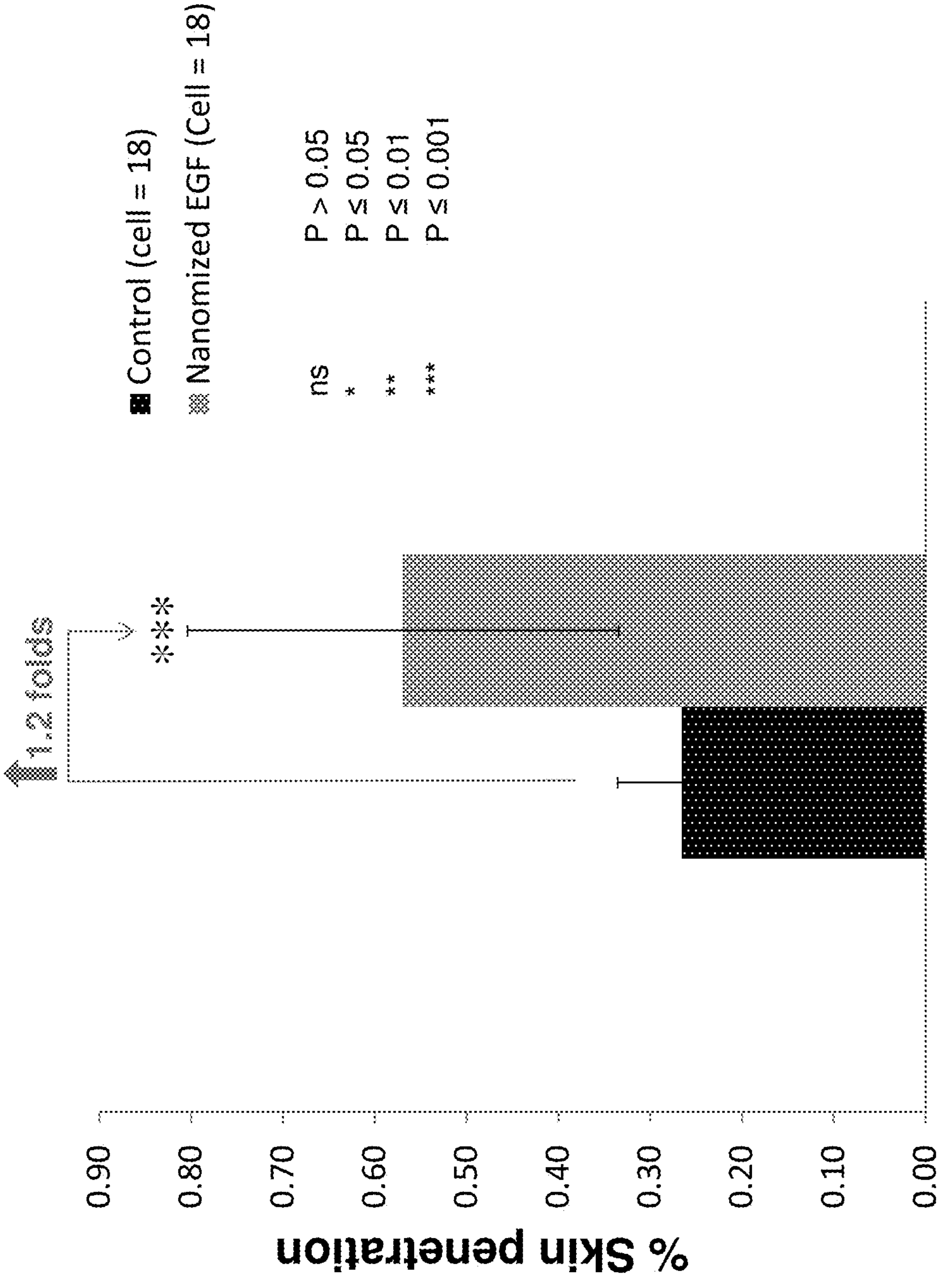
FIG. 24 is a graph showing percentage of nanomized EGF formulation and control in skin after 6 hours of diffusion cell experiment according to an embodiment of the presently claimed invention.

This is the skin penetration study of the optimized EGF nanoemulsion stated in Table 6. FIG. 24 shows the percentage of nanomized EGF formulation cream and control that penetrated to skin. The tested nanomized EGF formulation cream and control contained 0.02% of EGF. The nanomized EGF formulation was prepared from 0.067% of EGF nanoemulsion. The skin penetration of the nanomized EGF formulation is 1.2 fold higher than that of control when tested for 6 hours. This result indicates that skin penetration of EGF could be enhanced through this formulation for transdermal delivery. The average particle size of the tested EGF-nanoemulsion in this formulation was under 15 nm.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

The invention claimed is:

1. A chemical formulation for preparing a nanoemulsion, comprising:

isopropyl myristate;

polysorbate 80;

ethanol;

water; and an active ingredient selected from the group consisting of Schisandrin B and epidermal growth factor;

wherein a weight ratio of the water to the ethanol plus isopropyl myristate and polysorbate 80 is in a range of 3:7 to 2:8 and the nanoemulsion is an oil in water nanoemulsion.

2. The chemical formulation of claim 1, wherein the active ingredient is Schisandrin B, and the chemical formulation comprises 15-16wt % of isopropyl myristate, 37-39 wt % of polysorbate 80, 17-18 wt % of the ethanol, and 26-27 wt % of the water, and 0.6-1.5 wt % of the Schisandrin B.

3. The chemical formulation of claim 2, wherein the chemical formulation comprises 15.8 wt % of the isopropyl myristate, 38.4 wt % of the polysorbate 80, 17.7 wt % of the ethanol, 26.6 wt % of the water, and 1.5 wt % of the Schisandrin B.

4. A method for preparing a nanoernulsion with the chemical formulation of claim 1, comprising:

mixing the isopropyl myristate, the polysorbate 80, the ethanol, and the active ingredient to form a first mixture;

adding the water into the first mixture dropwisely to from a second mixture; and stirring the second mixture or homogenizing the second mixture to form the nanoemulsion.

5. The method of claim 4, wherein the step of stirring the second mixture comprises a magnetic stirring with a speed of 1000-2000 rpm for 2-20 min, or the step of homogenizing the second mixture comprises a homogenizing speed of 5000-20000 rpm for 2-20 min.

6. The chemical formulation of claim 1, further comprising a penetration enhancer.

7. The chemical formulation of claim 6, wherein the active ingredient is an epidermal growth factor, and the chemical formulation comprises 16-17 wt % of the isopropyl myristate, 39-42 wt % of the polysorbate 80, 18-19 wt % of the ethanol, and 19-21 wt % of the water, 0.0067-0.1333 wt % of the epidermal growth factor, and 0.5-4 wt % of the penetration enhancer.

8. The chemical formulation of claim 7, wherein the penetration enhancer is geraniol at a concentration of 0.5-1 wt %.

9. The chemical formulation of claim 8, wherein the chemical formulation comprises 17 wt % of the isopropyl myristate, 42 wt % of the polysorbate 80, 19 wt % of the ethanol, 21 wt % of the water, 0.067 wt % of the epidermal growth factor, and 1 wt % of geraniol.

10. A method for preparing a nanoemulsion with the chemical formulation of claim 6, comprising mixing the isopropyl myristate, the polysorbate 80, the ethanol, and the penetration enhancer to forma first mixture;

mixing the active ingredient and the water to form a second mixture;

adding the second mixture into the first mixture dropwisely to from a third mixture;

stirring the third mixture to form the nanoemulsion.

11. The method of claim 10, wherein the step of stirring the second mixture comprises a magnetic stirring with a speed of 1000-2000 rpm for 1-20 min.

12. A chemical formulation for preparing a nanoemulsion, comprising:

propylene glycol monocaprylate;

polysorbate 20;

a penetration enhancer;

water; and palmitoyl-pentapeptide-3;

wherein a weight ratio of the oil to the surfactant is in a range of 1:9 to 2:8 and the nanoemulsion is an oil in water nanoemulsion.

13. The chemical formulation of claim 12, wherein the chemical formulation comprises 1-3 wt % of the propylene glycol monocaprylate, 9-27 wt % of the polysorbate 20, 70-90 wt % of the water, 0.5-4 wt % of the penetration enhancer, and 0.05-6.7 wt % of the palmitoyl-pentapeptide-3.

14. The chemical formulation of claim 12, wherein the penetration enhancer is a phospholipid at a concentration of 0.25-0.5 wt %.

15. The chemical formulation of claim 14, wherein the chemical formulation comprises 1 wt % of the propylene glycol monocaprylate, 9 wt % of the polysorbate 20, 89 wt % of water, 0.67 wt % of the palmitoyl pentapeptide-3, and 0.5 wt % of the phospholipid.

16. A method for preparing a nanoemulsion with the chemical formulation of claim 12, comprising:

mixing the palmitoyl-pentapeptide-3, the propylene glycol monocaprylate, the polysorbate 20, and the penetration enhancer to form a first mixture;

adding the water into the first mixture dropwisely to from a second mixture; and stirring the second mixture or homogenizing the second mixture to form the nanoemulsion.

17. The method of claim 16, wherein the step of stirring the second mixture comprises a magnetic stirring with a speed of 500-1500 rpm for 1-10 min, or the step of homogenizing the second mixture comprises a homogenizing speed of 8000-20000 rpm for 1-10 min.

18. A chemical formulation for preparing a nanoemulsion, comprising:

15. 8 wt % of isopropyl myristate;

38. 4 wt % of polysorbate 80;

17. 7 wt % of ethanol;

26. 6 wt % of water; and 1.5 wt % of Schisandrin B;

wherein a weight ratio of the water to the ethanol plus the oil and the surfactant is 27:73 and the nanoemulsion is an oil in water nanoemulsion.

* * * * *

UNITED STATES PATENT AND TRADEMARK OFFICE
CERTIFICATE OF CORRECTION

PATENT NO. : 10,137,085 B2  
APPLICATION NO. : 14/624565  
DATED : November 27, 2018  
INVENTOR(S) : Huen et al.

Page 1 of 1

It is certified that error appears in the above-identified patent and that said Letters Patent is hereby corrected as shown below:

On the Title Page

Column 1, Item (72) should read:
--(72) Inventors: Ngar Yee HUEN, Hong Kong (HK); Sau Kuen Connie KWOK, Hong Kong (HK); Jinjie XU, Hong Kong (HK); Chun Him WONG, Hong Kong (HK); Min XiAO, Hong Kong (HK); Wah Kit CHEUK, Hong Kong (HK)--

Signed and Sealed this  
Twenty-seventh Day of August, 2019

Andrei Iancu  
*Director of the United States Patent and Trademark Office*